(12) United States Patent
Popovich et al.

(10) Patent No.: US 9,456,744 B2
(45) Date of Patent: Oct. 4, 2016

(54) APPARATUS FOR EYE TRACKING

(71) Applicants: Milan Momcilo Popovich, Leicester (GB); Jonathan David Waldern, Los Altos Hills, CA (US); Alastair John Grant, San Jose, CA (US)

(72) Inventors: Milan Momcilo Popovich, Leicester (GB); Jonathan David Waldern, Los Altos Hills, CA (US); Alastair John Grant, San Jose, CA (US)

(73) Assignee: DIGILENS, INC., Sunnyvale, CA (US)

( * ) Notice: Subject to any disclaimer, the term of this patent is extended or adjusted under 35 U.S.C. 154(b) by 42 days.

(21) Appl. No.: 14/409,875

(22) PCT Filed: May 10, 2013

(86) PCT No.: PCT/GB2013/000210
§ 371 (c)(1),
(2) Date: Dec. 19, 2014

(87) PCT Pub. No.: WO2013/167864
PCT Pub. Date: Nov. 14, 2013

(65) Prior Publication Data
US 2015/0289762 A1 Oct. 15, 2015

Related U.S. Application Data

(60) Provisional application No. 61/688,300, filed on May 11, 2012.

(51) Int. Cl.
*A61B 3/02* (2006.01)
*A61B 3/113* (2006.01)
(Continued)

(52) U.S. Cl.
CPC ............. *A61B 3/113* (2013.01); *G02B 6/0016* (2013.01); *G02B 27/0093* (2013.01); *G02B 27/017* (2013.01); *G02B 27/0172* (2013.01); *G02F 1/2955* (2013.01); *G02B 5/18* (2013.01); *G02B 6/34* (2013.01); *G02B 2027/014* (2013.01);
(Continued)

(58) Field of Classification Search
CPC .................................. A61B 3/113; A61B 3/00
USPC ...................... 351/210, 209; 385/10; 382/103
See application file for complete search history.

(56) References Cited

U.S. PATENT DOCUMENTS 3,804,496 A 4/1974 Crane et al.
4,028,725 A 6/1977 Lewis
(Continued)

FOREIGN PATENT DOCUMENTS

JP 2009036955 2/2009
WO 0016136 3/2000
(Continued)

OTHER PUBLICATIONS

International Search Report for PCT/GB2013/000210, Completed by the European Patent Office on Aug. 12, 2013, 3 Pages.
(Continued)

*Primary Examiner* — Hung Dang
(74) *Attorney, Agent, or Firm* — Brooks Kushman P.C.

(57) ABSTRACT

An eye tracker having a waveguide for propagating illumination light towards an eye and propagating image light reflected from at least one surface of an eye, a light source optically coupled to the waveguide, and a detector optically coupled to the waveguide. Disposed in the waveguide is at least one grating lamina for deflecting the illumination light towards the eye along a first waveguide path and deflecting the image light towards the detector along a second waveguide path.

20 Claims, 22 Drawing Sheets

(51) Int. Cl.
*G02B 27/01* (2006.01)
*G02B 27/00* (2006.01)
*G02F 1/295* (2006.01)
*F21V 8/00* (2006.01)
*G02B 5/18* (2006.01)
*G02F 1/1334* (2006.01)
*G02F 1/29* (2006.01)
*G02B 6/34* (2006.01)

(52) U.S. Cl.
CPC ............ *G02B 2027/0174* (2013.01); *G02B 2027/0187* (2013.01); *G02F 1/13342* (2013.01); *G02F 2001/294* (2013.01); *G02F 2201/16* (2013.01); *G02F 2201/30* (2013.01); *G02F 2201/307* (2013.01); *G02F 2203/24* (2013.01); *G02F 2203/28* (2013.01); *G02F 2203/62* (2013.01)

(56) References Cited

U.S. PATENT DOCUMENTS

| | | |
|---|---|---|
| 4,852,988 A | 8/1989 | Velez et al. |
| 5,410,376 A | 4/1995 | Cornsweet et al. |
| 5,751,452 A | 5/1998 | Tanaka et al. |
| 5,942,157 A | 8/1999 | Sutherland et al. |
| 6,351,273 B1 | 2/2002 | Lemelson et al. |
| 7,542,210 B2 | 6/2009 | Chirieleison, Sr. |
| 8,929,589 B2 * | 1/2015 | Publicover ......... G06K 9/00604 382/103 |
| 2002/0167462 A1 | 11/2002 | Lewis et al. |
| 2011/0019874 A1 | 1/2011 | Jarvenpaa et al. |
| 2013/0077049 A1 | 3/2013 | Bohn |
| 2013/0250207 A1 | 9/2013 | Bohn |
| 2014/0104665 A1 | 4/2014 | Popovich et al. |
| 2014/0140653 A1 | 5/2014 | Brown et al. |

FOREIGN PATENT DOCUMENTS

| | | |
|---|---|---|
| WO | 2007085682 | 8/2007 |
| WO | 2007130130 | 11/2007 |
| WO | 2008100545 | 8/2008 |
| WO | 2009101238 | 8/2009 |
| WO | 2010125337 | 11/2010 |
| WO | 2011051660 | 5/2011 |
| WO | 2013027006 | 2/2013 |
| WO | 2013049012 | 4/2013 |
| WO | 2013163347 | 10/2013 |
| WO | 2013167864 | 11/2013 |

OTHER PUBLICATIONS

International Search Report for PCT/GB2014/000197, Completed by the European Patent Office on Jul. 31, 2014, 3 Pages.
International Search Report for PCT/GB2015/000274, Completed by the European Patent Office on Jan. 7, 2016, 4 Pages.

* cited by examiner

APPARATUS FOR EYE TRACKING

CROSS-REFERENCE TO RELATED APPLICATION

This application is the U.S. national phase of PCT Application No. PCT/GB2013/000210 filed on May 10, 2013, which claims the benefit of U.S. Provisional Application No. 61/688,300 filed on May 11, 2012, the disclosures of which are incorporated in their entirety by reference herein.

The following patent applications are incorporated by reference herein in their entireties:

U.S. Provisional Patent Application No. 61/687,436 with filing date 25 Apr. 12 entitled WIDE ANGLE COLOUR HEAD MOUNTED DISPLAY.

U.S. Provisional Patent Application No. 61/689,907 with filing date 25 Apr. 12 entitled HOLOGRAPHIC HEAD MOUNTED DISPLAY WITH IMPROVED IMAGE UNIFORMITY.

U.S. Provisional Application No. 61/796,632 with filing date 16 Oct. 2012 entitled TRANSPARENT DISPLAYS BASED ON HOLOGRAPHIC SUBSTRATE GUIDED OPTICS.

U.S. Provisional Application No. 61/849,853 with filing date 4 Feb. 2013 entitled TRANSPARENT WAVEGUIDE DISPLAY.

PCT Application No.: US2008/001909, with International Filing Date: 22 Jul. 2008, entitled LASER ILLUMINATION DEVICE.

PCT Application No.: US2006/043938, entitled METHOD AND APPARATUS FOR PROVIDING A TRANSPARENT DISPLAY.

PCT Application No.: PCT/GB2010/001982 entitled COMPACT EDGE ILLUMINATED EYEGLASS DISPLAY.

PCT Application No.: PCT/GB2012/000680, entitled IMPROVEMENTS TO HOLOGRAPHIC POLYMER DISPERSED LIQUID CRYSTAL MATERIALS AND DEVICES.

PCT Application No.: PCT/GB2010/000835 entitled COMPACT HOLOGRAPHIC EDGE ILLUMINATED EYEGLASS DISPLAY.

U.S. Pat. No. 6,115,152 entitled HOLOGRAPHIC ILLUMINATION SYSTEM.

BACKGROUND OF THE INVENTION

This invention relates to an eye tracking sensor, and more particularly to an eye tracker using electrically switchable gratings.

Eye tracking is important in Head Mounted Displays (HMDs) because it can extend the pilot's ability to designate targets well beyond the head mobility limits. Eye tracking technology based on projecting IR light into the users eye and utilizing the primary Purkinje (corneal) reflection and the pupil-masked retina reflection have been around since the 1980's. The method tracks the relative motion of these images in order to establish a vector characterizing the point of regard. Most eye trackers have employed flat beam splitters in front of the users' eyes and relatively large optics to image the reflections onto a sensor (generally a CCD or CMOS camera).

There is much prior art in the patent and scientific literature including the following United States filings:
1. United Stated Patent Application Publication No. US2011019874(A1) by Levola et al entitled DEVICE AND METHOD FOR DETERMINING GAZE DIRECTION;
2. U.S. Pat. No. 5,410,376 by Comsweet entitled EYE TRACKING METHOD AND APPARATUS;
3. U.S. Pat. No. 3,804,496 by Crane et al entitled TWO DIMENSIONAL EYE TRACKER AND METHOD FOR TRACKING AN EYE TWO DIMENSIONAL EYE TRACKER AND METHOD FOR TRACKING AN EYE;
4. U.S. Pat. No. 4,852,988 by Velez et al entitled VISOR AND CAMERA PROVIDING A PARALLAX-FREE FIELD-OF-VIEW IMAGE FOR A HEAD-MOUNTED EYE MOVEMENT MEASUREMENT SYSTEM;
5. U.S. Pat. No. 7,542,210 by Chirieleison entitled EYE TRACKING HEAD MOUNTED DISPLAY;
6. United Stated Patent Application Publication No. US 2002/0167462 A1 by Lewis entitled PERSONAL DISPLAY WITH VISION TRACKING; and
7. U.S. Pat. No. 4,028,725 by Lewis entitled HIGH RESOLUTION VISION SYSTEM.

The exit pupil of these trackers is generally limited by either the size of the beamsplitter or the first lens of the imaging optics. In order to maximize the exit pupil, the imaging optics are positioned close to the beamsplitter, and represent a vision obscuration and a safety hazard. Another known limitation with eye trackers is the field of view, which is generally limited by the illumination scheme in combination with the geometry of the reflected images off the cornea. The cornea is an aspheric shape of smaller radius that the eye-ball. The cornea reflection tracks fairly well with angular motion until the reflected image falls off the edge of the cornea and onto the sclera. The need for beam splitters and refractive lenses in conventional eye trackers results in a bulky component that is difficult to integrate into a (HMD). The present invention addresses the need for a slim, wide field of view, large exit pupil, high-transparency eye tracker for HMDs.

The inventors have found the diffractive optical elements offer a route to providing compact, transparent, wide field of view eye trackers. On important class of diffractive optical elements is based on Switchable Bragg Gratings (SBGs). SBGs are fabricated by first placing a thin film of a mixture of photopolymerizable monomers and liquid crystal material between parallel glass plates. One or both glass plates support electrodes, typically transparent indium tin oxide films, for applying an electric field across the film. A volume phase grating is then recorded by illuminating the liquid material (often referred to as the syrup) with two mutually coherent laser beams, which interfere to form a slanted fringe grating structure. During the recording process, the monomers polymerize and the mixture undergoes a phase separation, creating regions densely populated by liquid crystal micro-droplets, interspersed with regions of clear polymer. The alternating liquid crystal-rich and liquid crystal-depleted regions form the fringe planes of the grating. The resulting volume phase grating can exhibit very high diffraction efficiency, which may be controlled by the magnitude of the electric field applied across the film. When an electric field is applied to the grating via transparent electrodes, the natural orientation of the LC droplets is changed causing the refractive index modulation of the fringes to reduce and the hologram diffraction efficiency to drop to very low levels. Note that the diffraction efficiency of the device can be adjusted, by means of the applied voltage, over a continuous range. The device exhibits near 100% efficiency with no voltage applied and essentially zero efficiency with a sufficiently high voltage applied. In certain types of HPDLC devices magnetic fields may be used to control the LC orientation. In certain types of HPDLC phase separation of the LC material from the polymer may be accomplished to such a degree that no discernible droplet structure results.

SBGs may be used to provide transmission or reflection gratings for free space applications. SBGs may be implemented as waveguide devices in which the HPDLC forms either the waveguide core or an evanescently coupled layer in proximity to the waveguide. In one particular configuration to be referred to here as Substrate Guided Optics (SGO) the parallel glass plates used to form the HPDLC cell provide a total internal reflection (TIR) light guiding structure. Light is "coupled" out of the SBG when the switchable grating diffracts the light at an angle beyond the TIR condition. SGOs are currently of interest in a range of display and sensor applications. Although much of the earlier work on HPDLC has been directed at reflection holograms transmission devices are proving to be much more versatile as optical system building blocks.

Typically, the HPDLC used in SBGs comprise liquid crystal (LC), monomers, photoinitiator dyes, and coinitiators. The mixture frequently includes a surfactant. The patent and scientific literature contains many examples of material systems and processes that may be used to fabricate SBGs. Two fundamental patents are: U.S. Pat. No. 5,942, 157 by Sutherland, and U.S. Pat. No. 5,751,452 by Tanaka et al. both filings describe monomer and liquid crystal material combinations suitable for fabricating SBG devices.

One of the known attributes of transmission SBGs is that the LC molecules tend to align normal to the grating fringe planes. The effect of the LC molecule alignment is that transmission SBGs efficiently diffract P polarized tight (ie light with the polarization vector in the plane of incidence) but have nearly zero diffraction efficiency for S polarized tight (ie light with the polarization vector normal to the plane of incidence. Transmission SBGs may not be used at near-grazing incidence as the diffraction efficiency of any grating for P polarization falls to zero when the included angle between the incident and reflected light is small.

There is a requirement for a compact, lightweight eye tracker with a large field of view, and a high degree of transparency to external light.

SUMMARY OF THE INVENTION

It is a first object of the invention to provide a compact, lightweight eye tracker with a large field of view, and a high degree of transparency to external light.

It is a second object of the invention to provide a compact, lightweight eye tracker with a large field of view, and a high degree of transparency to external light implemented in a thin optical waveguide.

The objects of the invention are achieved in one embodiment of the invention in which there is provided a eye tracker comprising: a waveguide for propagating illumination light towards an eye and propagating image light reflected from at least one surface of an eye; a light source optically coupled to the waveguide; a detector optically coupled to the waveguide. Disposed in the waveguide is at least one grating lamina for deflecting the illumination light towards the eye along a first waveguide path and deflecting the image light towards the detector along a second waveguide path.

In one embodiment of the invention the first and second waveguide paths are in opposing directions.

In one embodiment of the invention at least one portion of the at least one grating lamina deflects the illumination light out of the first waveguide path and at least one portion of the at least one grating lamina deflects the image light into the second waveguide path.

In one embodiment of the invention the grating lamina comprises a multiplicity of electrically switchable elements each having a diffracting state and a non diffracting state. The at least one portion of the at least one grating lamina is a grating element in its diffracting state.

In one embodiment of the invention the electrically switchable elements are elongate with longer dimension aligned perpendicular to at least one of the first and second waveguide paths.

In one embodiment of the invention the at least one grating lamina comprises an illumination grating for deflecting the illumination light in the first waveguide path towards the eye and an imaging grating for deflecting the image light into the second waveguide path.

In one embodiment of the invention at least one grating lamina further comprises at least one of an input grating for deflecting illumination light from the source into the first waveguide path and an output grating for deflecting the image light out of the second waveguide path towards the detector.

In one embodiment of the invention the eye tracker further comprises an image sampling grating overlaying the output grating. The image sampling grating comprises a linear array of switchable grating elements. Each grating element when in its diffracting state samples a portion of the light in the waveguide and deflects it along the image sampling grating towards the detector.

In one embodiment of the invention the eye tracker further comprises an illumination sampling grating overlaying the input grating. The illumination sampling grating is optically coupled to the light source. The illumination sampling grating comprises a linear array of switchable grating elements. Each grating element when in its diffracting state deflects light from the illumination sampling grating into the waveguide.

In one embodiment of the invention the illumination grating abuts an upper or lower edge of the imaging grating along the first waveguide path.

In one embodiment of the invention the illumination grating comprises first and second gratings disposed adjacent upper and lower edges of the imaging grating along the first waveguide path.

In one embodiment of the invention the imaging grating comprises a first array of switchable elongate beam deflection grating elements and an overlapping second array of switchable elongate beam deflection grating elements. The elements of the first and second arrays are disposed with their longer dimensions orthogonal.

In one embodiment of the invention the illumination grating is a linear array of elongate switchable beam deflection elements with longer dimension aligned perpendicular to the first waveguide path.

In one embodiment of the invention the at least one grating lamina is one of a switchable Bragg grating, a switchable grating recorded in a reverse mode holographic polymer dispersed liquid crystal, or a non switching Bragg grating.

In one embodiment of the invention the image light is speckle.

In one embodiment of the invention the eye surface providing the image light is at least one of the cornea, lens, iris, sclera and retina.

In one embodiment of the invention the detector is a two dimensional array.

In one embodiment of the invention the at least one grating lamina encodes optical power.

In one embodiment of the invention the detector is connected to an image processing apparatus for determining at least one spatio-temporal characteristic of an eye movement.

In one embodiment of the invention the image light is a Purkinje reflection.

In one embodiment of the invention the source is a laser.

In one embodiment of the invention source is a light emitting diode.

In one embodiment of the invention the illumination grating provides collimated light.

In one embodiment of the invention the illumination grating provides divergent light.

In one embodiment of the invention the imaging grating encodes optical power.

In one embodiment of the invention the illumination grating encodes optical power.

In one embodiment of the invention the illumination, imaging, input and output gratings are co planar.

In one embodiment of the invention the input and illumination gratings lie in a first plane and the imaging and output gratings lie in a second plane parallel to the first plane.

A more complete understanding of the invention can be obtained by considering the following detailed description in conjunction with the accompanying drawings, wherein like index numerals indicate like parts. For purposes of clarity, details relating to technical material that is known in the technical fields related to the invention have not been described in detail.

DETAILED DESCRIPTION OF THE INVENTION

Figure 1:
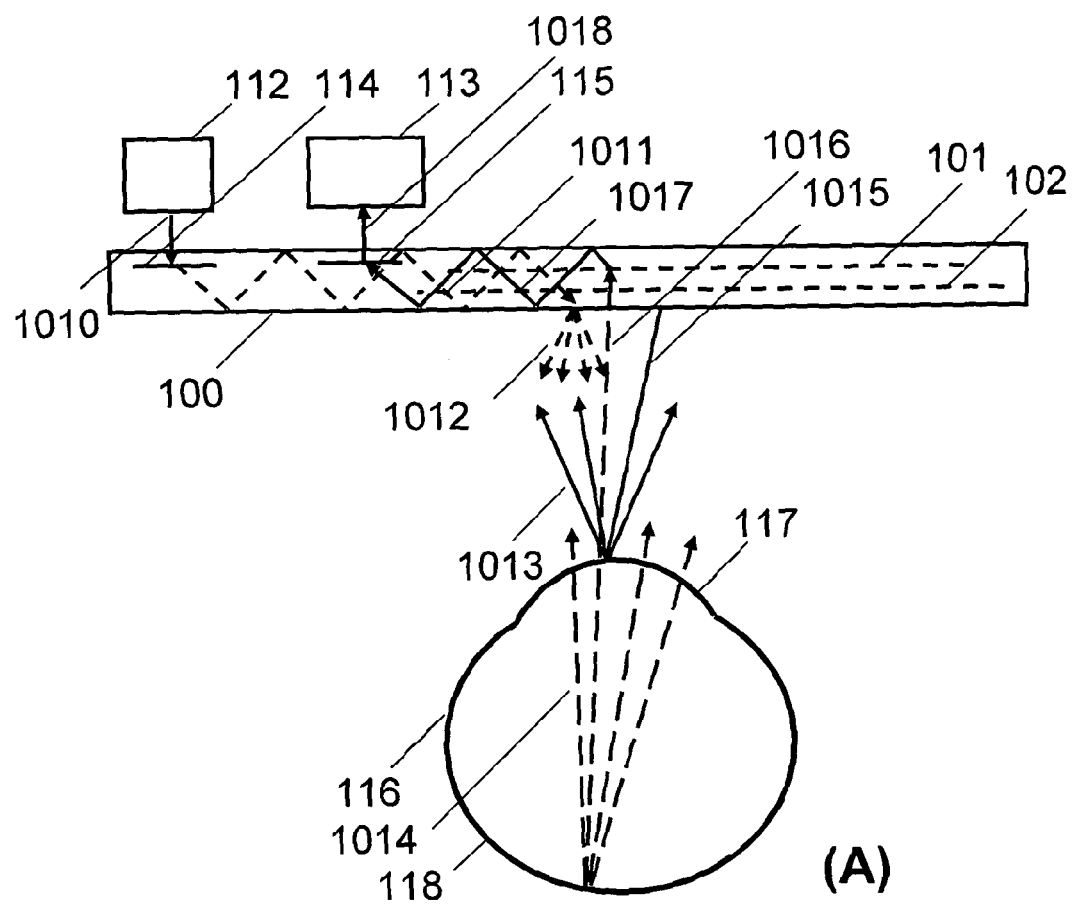
FIG. 1A is a schematic plan view of an eye tracker shown in relation to a human eye in one embodiment of the invention
FIG. 1B is a schematic front elevation view showing elongate grating elements used in the imaging grating in one embodiment of the invention.
FIG. 1C is a schematic front elevation view showing a two dimensional array of grating elements used in the imaging grating in one embodiment of the invention.
Figure 1:
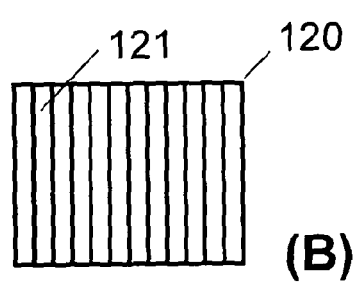
Figure 1:
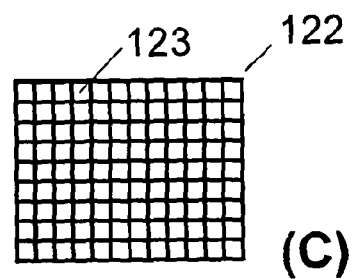

The invention will now be further described by way of example only with reference to the accompanying drawings. It will apparent to those skilled in the art that the present invention may be practiced with some or all of the present invention as disclosed in the following description. For the purposes of explaining the invention well-known features of optical technology known to those skilled in the art of optical design and visual displays have been omitted or simplified in order not to obscure the basic principles of the invention. Unless otherwise stated the term "on-axis" in relation to a ray or a beam direction refers to propagation parallel to an axis normal to the surfaces of the optical components described in relation to the invention. In the following description the terms light, ray, beam and direction may be used interchangeably and in association with each other to indicate the direction of propagation of light energy along rectilinear trajectories. Parts of the following description will be presented using terminology commonly employed by those skilled in the art of optical design. It should also be noted that in the following description of the invention repeated usage of the phrase "in one embodiment" does not necessarily refer to the same embodiment.

The proposed eye tracker aims to satisfy a suite of challenging requirements. Since it will eventually be integrated into a head-worn color display, it should make minimum impact on the overall optical performance. The inventors' design goals are: a field of view (FOV) of 60° horizontal×48° vertical; 17 mm eye relief; and eye motion box/exit pupil (20 mm.×10-15 mm). Moreover, the eye tracker must satisfy eye safety requirements for near-eye visual displays with regard to weight (minimal), center of gravity (ergonomic), and profile. Furthermore it should not compromise: pixel resolution, see-through (≥90%) and power consumption (minimal).

Eye Trackers based on classical Purkinje imaging methods suffer from high latency resulting mainly from the large delay incurred by feature recognition and tracking algorithms. The inventors are strongly motivated by a desire to develop an eye tracker that firstly simplifies the image processing problems of classical eye tracking that often result in unacceptably high latency and secondly can make use of relatively unsophisticated detector technology. Ideally the detector technology would be equivalent in specification to that used in the infrared mouse a device which is now ubiquitous and more importantly capable of being manufactured using sub dollar components. Although the present invention may be used to track eye movements using any type of reflection from any surfaces of the eye (including reflections from multiple surfaces and scatter from the optical media inside the eye) the inventors believe that tracking laser speckle reflected from the cornea, retina and other surfaces may offer significant. The inventors believe that detecting and processing speckle images is more efficient than conventional video based technology in terms of detector resolution, processing overhead and power consumption.

An eye tracker according to the principles of the invention provides an infrared illumination channel for delivering infrared illumination to the eye and an imaging channel for forming an image of the eye at a sensor. In one embodiment of the invention illustrated in FIGS. 1-2, the eye tracker comprises a waveguide 100 for propagating illumination light towards an eye 116 and propagating image light reflected from at least one surface of an eye; a light source 112 optically coupled to the waveguide; and a detector 113 optically coupled to the waveguide. Disposed in the waveguide are: at least one input grating 114 for deflecting illumination light from the source into a first waveguide path; at least one illumination grating 102 for deflecting the illumination light towards the eye; at least one imaging grating 101 for deflecting the image light into a second waveguide path; and at least one output grating 115 for deflecting the image light towards the detector. The inventors also refer to the waveguide 100 as the DigiLens. The illumination and imaging gratings are arrays of switchable beam deflection grating elements with the preferred grating technology being a SBG as described above. In one embodiment of the invention shown in FIG. 1B the grating elements in the imaging grating 120 are elongate as indicated by 121 with longer dimension orthogonal to the beam propagation direction. In one embodiment of the invention shown in FIG. 1C the imaging grating may comprise a two dimensional array 122 of elements 123 each having optical power in two orthogonal planes. Typically the first and second waveguide paths, that is, the imaging and illumination paths in the waveguide are in opposing directions as illustrated in FIG. 1A. The illumination light will typically be fully collimated while the image light will have some divergence of angle determined by the scattering angle from eye services, the angular bandwidth of the gratings and the numerical aperture of the grating elements. As will be discussed later, in one embodiment the imaging and illumination gratings are provided by a single grating with the illumination and imaging ray paths. Where separate imaging and illumination gratings are used the two gratings may employ different TIR angles within the waveguide. This is advantageous in terms of avoiding the risk of cross coupling of illumination light into the detector and image light into the light source.

In FIG. 1A the illumination light path is illustrated by the light 1010 from the source which is directed into a TIR path 1011 by the input prating and diffracted out of the waveguide as the light generally indicated by 1012. Typically the eye tracker will have a pupil of size 20-30 mm. Since the eye tracker will usually be implemented as part of a HMD its pupil should desirably match that of the HMD. FIG. 1a shows return light 1013 reflected from the front surface of the cornea 117 and light 1014 reflected from the retina 118. The corneal and retinal image light enters the waveguide along tray paths such 1015, 1116 and is deflected into a TIR path such as 1017 by an active element of the imaging grating which is switching one element at a time. The light 1017 is deflected into a ray path 1018 toward the detector by the output grating. The detector reads out the image signal in synchronism with the switching of the SBG lens array elements. The detector is connected to an image processing apparatus for determining at least one spatio-temporal characteristic of an eye movement. The image processor, which is not illustrated, detects pre-defined features of the back-scattered signals from the cornea and retina. For example, the image processor may be used to determine the centroid of an eye feature such as the pupil. Other trackable features of the eye will be well known to those skilled in arts of eye tracker design and visual optics.

The eye surfaces used for tracking are not necessarily limited to the front surface of the cornea and the retina. The invention can be applied using reflections from any of the surfaces of the lens, iris and sclera including any of the reflections normally referred to as Purkinje reflections. In one particularly important embodiment of the invention to be discussed later the light reflected from the eye is speckle. The speckle may arise from reflections at any of the above surfaces or from the bulk medium of the cornea lens and other parts of the eye.

Advantageously, the light source is a laser emitting in the infrared band. Typically, the laser emits at a wavelength in the range 785-950 nm. The choice of wavelength will depend on laser efficiency, signal to noise and eye safety considerations. Light Emitting Diodes (LEDs) may also be used. In one embodiment of the invention the detector is a two dimensional array. However other detector may be used including linear arrays and analogue devices such as position sensing detectors.

In the embodiment shown in FIG. 1 the illumination grating provides divergent light. In alternative embodiments of the invention the illumination grating provides collimated light.

The gratings may be implemented as lamina within or adjacent an external surface of the waveguide. Advantageously the gratings are switchable Bragg gratings (SBGs). In certain embodiments of the invention passive gratings may be used. However, passive gratings lack the advantage of being able to direct illumination and collect image light from precisely defined areas of the pupil. In one embodiment the gratings are reverse mode SBGs. Although the invention is discussed in relation to transmission gratings it should be apparent to those skilled in the art that equivalent embodiments using reflection gratings should be feasible in most cases. The gratings may be surface relief gratings. However, such gratings will be inferior to Bragg gratings in terms of their optical efficiency and angular/wavelength selectivity.

Figure 2:
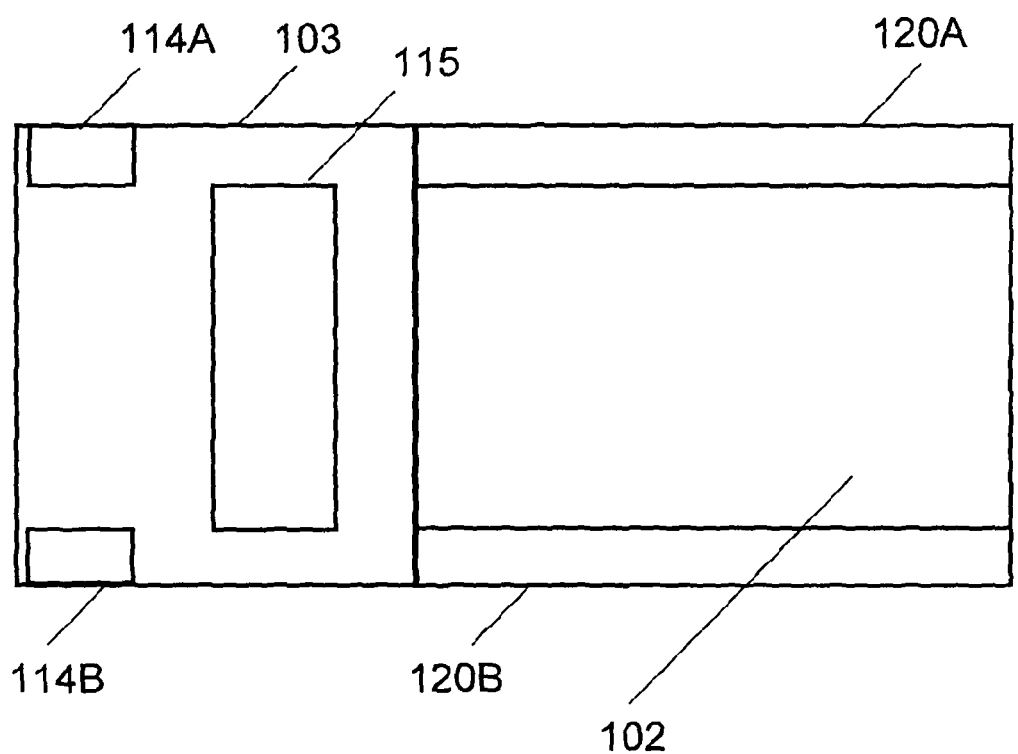
FIG. 2 is a schematic plan view of the eye tracker shown the imaging and illumination gratings and input and output gratings in one embodiment of the invention.

The input and illumination gratings may be configured in many different ways. FIG. 2 is a schematic plan view showing one possible implementation for use with the embodiment of FIG. 1. Here input grating comprises two grating elements 114A,114B and the illumination grating is also divided into the upper and lower gratings 120A,120B each providing narrow beam deflecting grating strips above and below the imaging grating 102. The detector grating 115 is also indicated. Since the guided beams in the input and illumination grating are collimated and likewise the guided beams in the imaging and detector gratings there is no cross talk between the two regions of the waveguide.

Figure 3:
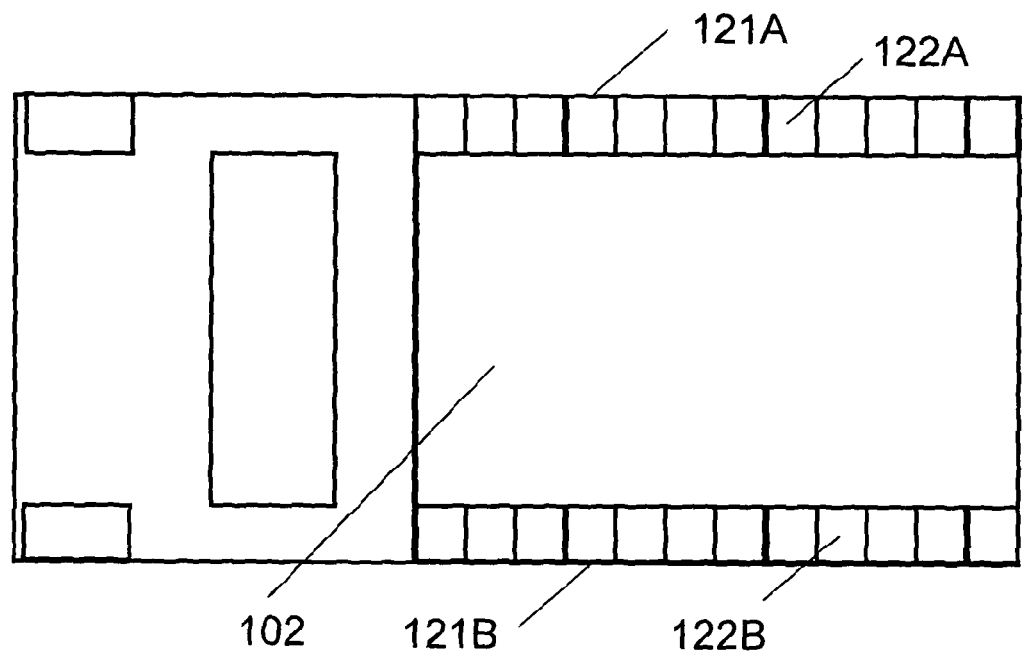
FIG. 3 is a schematic plan view of the eye tracker shown the imaging and illumination gratings and input and output gratings in one embodiment of the invention.
Figure 4:
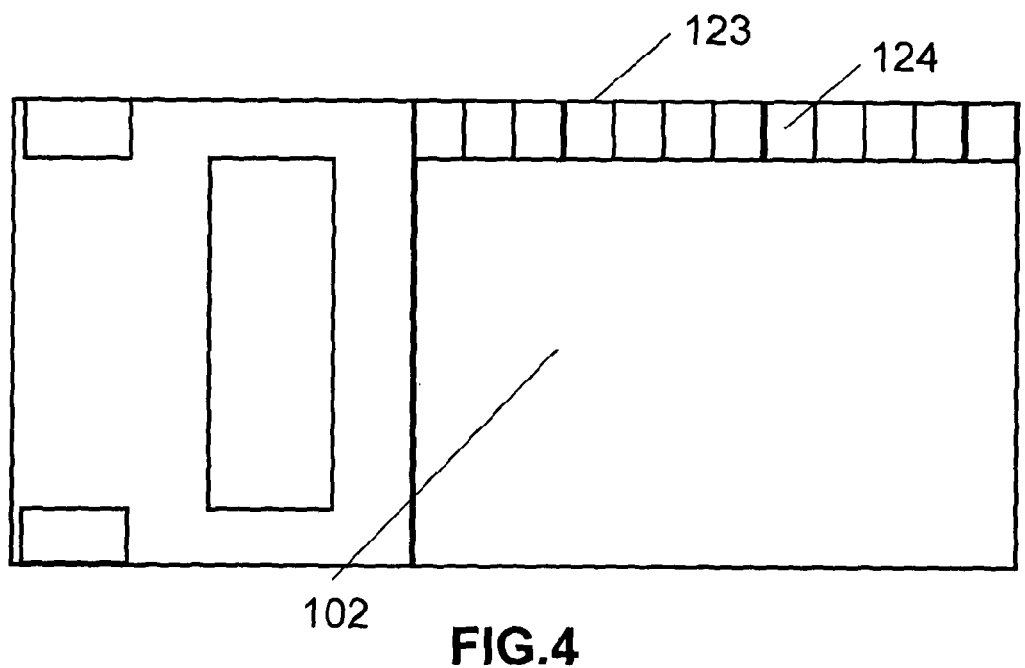
FIG. 4 is a plan view of the eye tracker shown the imaging and illumination gratings and input and output gratings in one embodiment of the invention.

In the embodiment of the invention shown in FIGS. 3-4 similar to the one of FIG. 2 the upper and lower illumination grating may be arrays of switchable grating elements 121A, 121B comprised switchable grating elements such as 122A, 122B. The SBG deflector arrays scroll illumination across the exit pupil in step with the activation of the imaging grating elements. Finally in the embodiment of FIG. 4 the illumination grating comprises just one strip 123 containing elements 124 at the top edge of the imaging grating.

The invention does not assume any particular configuration of the grating elements. It is important to note that the SBGs are formed as continuous lamina. Hence the illumination gratings elements may be considered to be part of the imaging grating. This is a significant advantage in terms of fabrication and overall form factor. In embodiment where the illumination grating is split into two elements the input laser light may be provided by one laser with the upper and lower beam being provided by a beam splitting means. Alternatively, two separate laser modules may be used to provide light that is coupled into the waveguide via the input gratings 114A,114B are illustrated in FIGS. 3-4. The invention does not assume any particular method for providing the laser input illumination or coupling the laser light into the waveguide. Many alternative schemes should be apparent to those skilled in the art of optical design.

Figure 5:
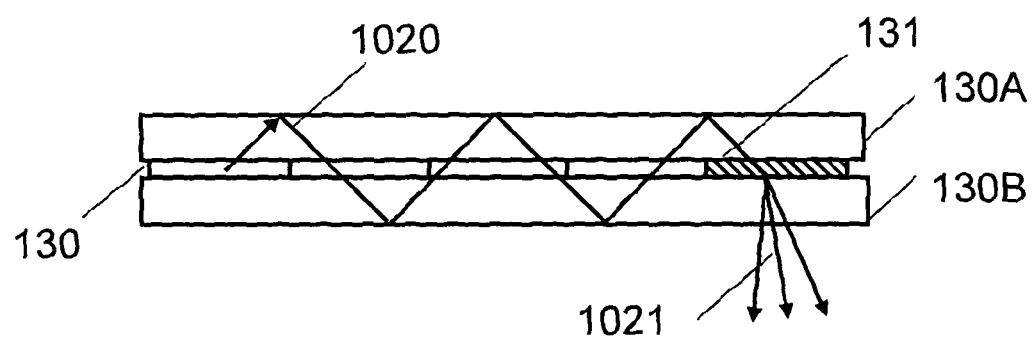
FIG. 5 is a schematic cross section view of an illumination grating used in one embodiment of the invention.

The illumination grating may provide illumination light of any beam geometry. For examples the light may be a parallel beam emitted normally to the surface of the eye tracker waveguide. The illuminator grating is illustrated in more detail in the schematic side elevation view of FIG. 5. The SBG linear array 130 is sandwiched between transparent substrates 130A,130B. Note that the substrate layers extended to cover the entire waveguide and therefore also act as the substrates for the imaging grating. Advantageously, the ITO layers are applied to the opposing surfaces of the substrates with at least one ITO layer being patterned such that SBG elements may be switched selectively. The substrates and SBG array together form a light guide. Each SBG array element has a unique optical prescription designed such that input light incident in a first direction is diffracted into output light propagating in a second direction. FIG. 5 shows TIR illumination beam 1020 being deflected by the active element 131 to provide divergent illumination light 1021. The geometrical optics of has been simplified for the sake of simplifying the description.

Figure 6:
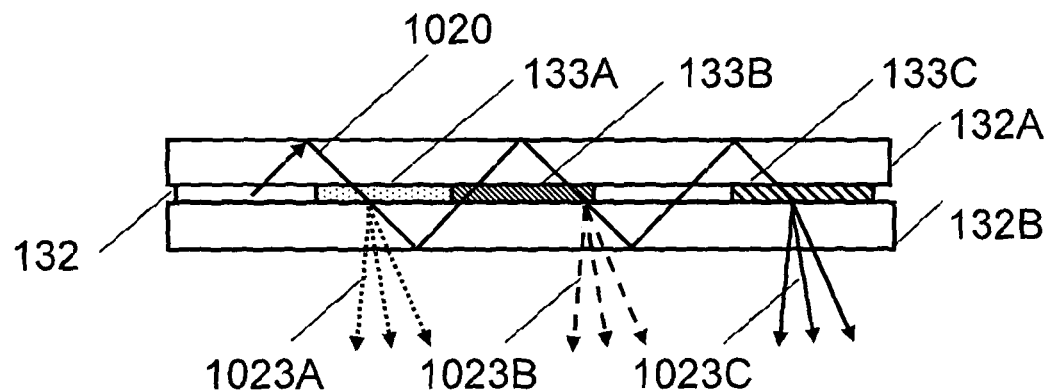
FIG. 6 is a schematic cross section view of an illumination grating used in one embodiment of the invention.
Figure 7:
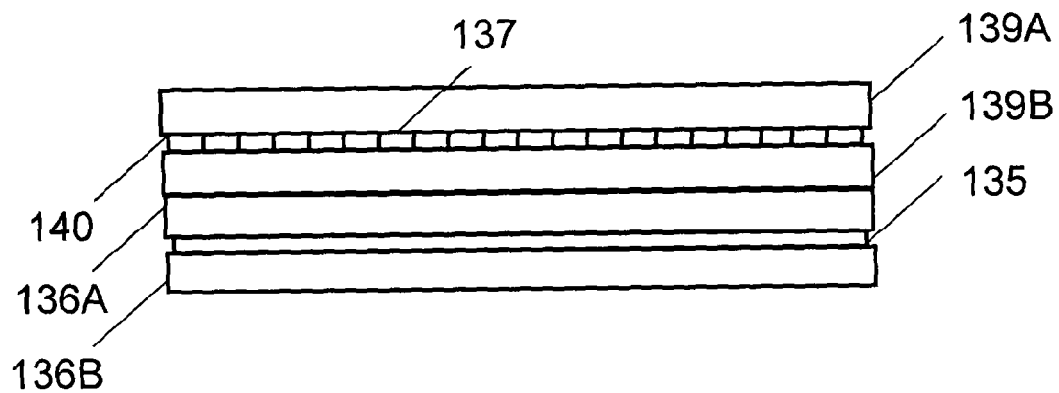
FIG. 7 is a schematic cross section view of a first aspect of an imaging grating used in one embodiment of the invention.

An alternative embodiment of the linear deflector array is shown in the schematic side elevation view of FIG. 6. In this cases the array 132 sandwich by substrates 132A,132B is based on a lossy grating that diffracts incrementally increasing fractions of the guided beam out of the waveguide towards the eye. Beam portions 1023A-1023C diffracted by the grating elements 133A-133C are illustrated. Typically the index modulation of the grating elements will be designed to provide uniform extraction along the array and hence uniform output illumination.

Advantageously, the illumination grating elements encode optical power to provide sufficient beam spread to fill the exit pupil with light. A similar effect may be produce by encode diffusion characteristics into the gratings. The apparatus may further comprise an array of passive holographic beam-shaping diffusers applied to the substrate overlaps the linear SBG arrays to enhance the diffusion. Methods for encoding beam deflection and diffusion into diffractive devices are well known to those skilled in the art of diffractive optics. Cross talk between the imaging and illumination channels is overcome by configuring the SBGs such that the illumination TIR path within the eye tracker lies outside the imaging TIR path.

Figure 8:
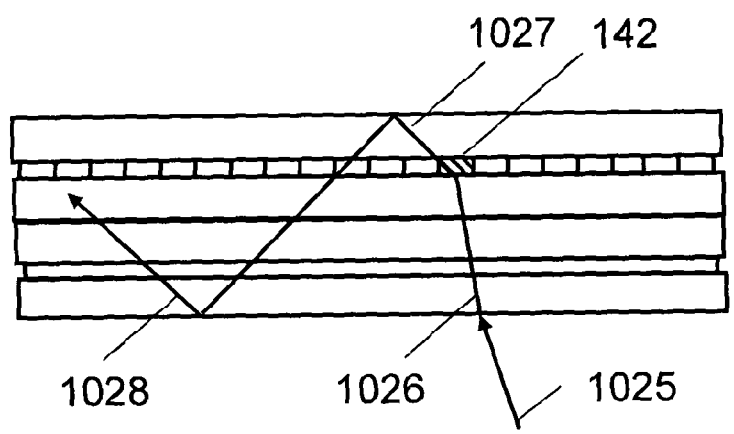
FIG. 8 is a schematic cross section view of a second aspect of an imaging grating used in one embodiment of the invention.
Figure 9:
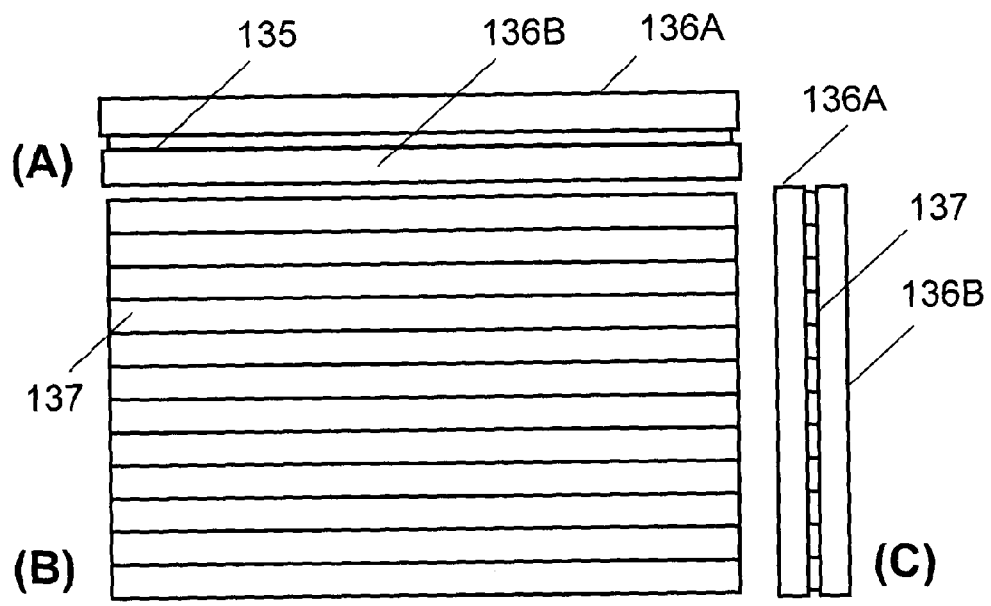
FIG. 9A is a schematic top elevation view of a first layer of a two layer imaging grating in one embodiment of the invention.
FIG. 9B is a schematic plan view of a first layer of a two layer imaging grating in one embodiment of the invention.
FIG. 9C is a schematic side elevation view of a first layer of a two layer imaging grating in one embodiment of the invention.
Figure 10:
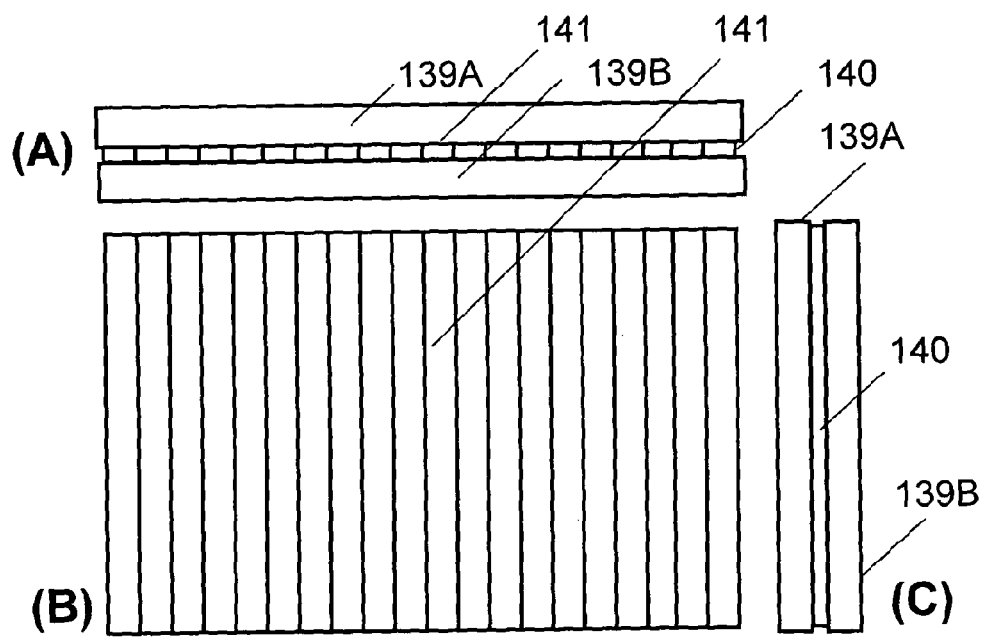
FIG. 10A is a schematic top elevation view of a second layer of a two layer imaging grating in one embodiment of the invention.
FIG. 10B is a schematic plan view of a second layer of a two layer imaging grating in one embodiment of the invention.
FIG. 10C is a schematic side elevation view of a second layer of a two layer imaging grating in one embodiment of the invention.

In one embodiment of the invention the imaging grating may also encode optical power. A two layer SBG imaging grating that encodes optical power is illustrated in FIGS. 7-10. The arrays are shown in their stacked configuration in FIG. 7. The substrates 136A,136B and 139A,139B together provide the imaging waveguide as illustrated in FIG. 8 where the ray path from the eye into the waveguide via an activated SBG element 42 is represented by rays 1025-1028. The arrays are shown in front, plan and side elevation views in FIGS. 9-10. The arrays comprise linear arrays of column elements each having the optical characteristics of a cylindrical lens. The column vectors in the two arrays are orthogonal. The first array comprises the SBG array 135 sandwiched by the substrates 136A,136B with one particular element 137 being indicated. The second array comprises the SBG array 40 sandwiched by the substrates 139A,139B with one particular element 141 being indicated.

Figure 11:
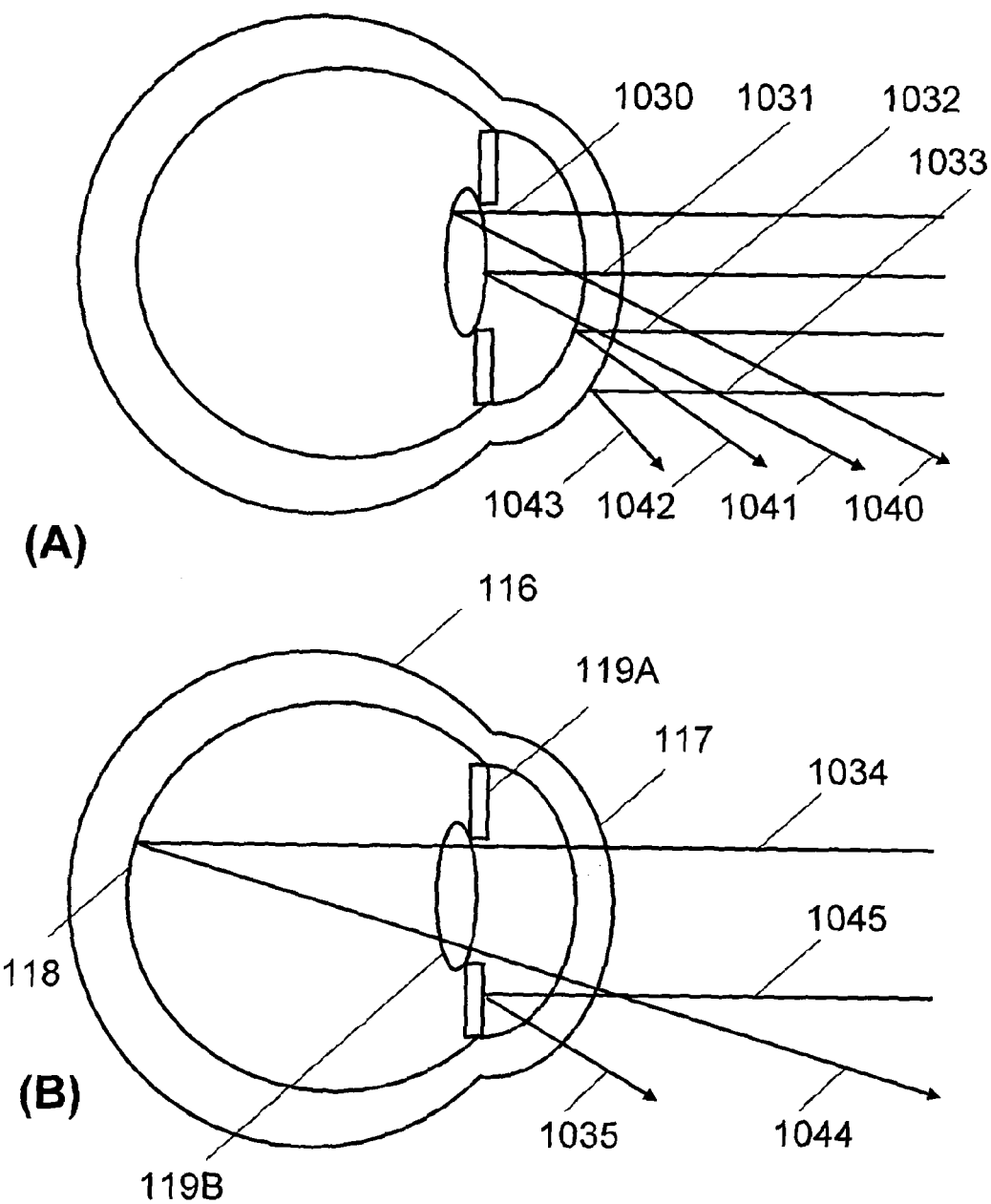
FIG. 11A is a schematic cross view of the human eye illustrating the formation of the Purkinje images.
FIG. 11B is a schematic cross view of the human eye illustrating reflections from the retina and iris.

FIG. 11A illustrates the principles of the formation of the first four Purkinje images corresponding to reflections off the front of the cornea 1033,1043; the back of the cornea 1032, 1042; the front of the eye lens 1031,1041; and the back of the eye lens 1030,1040. FIG. 11B illustrates the formation of images of the retina 1034,1044 and the iris 1035,1045.

Figure 12:
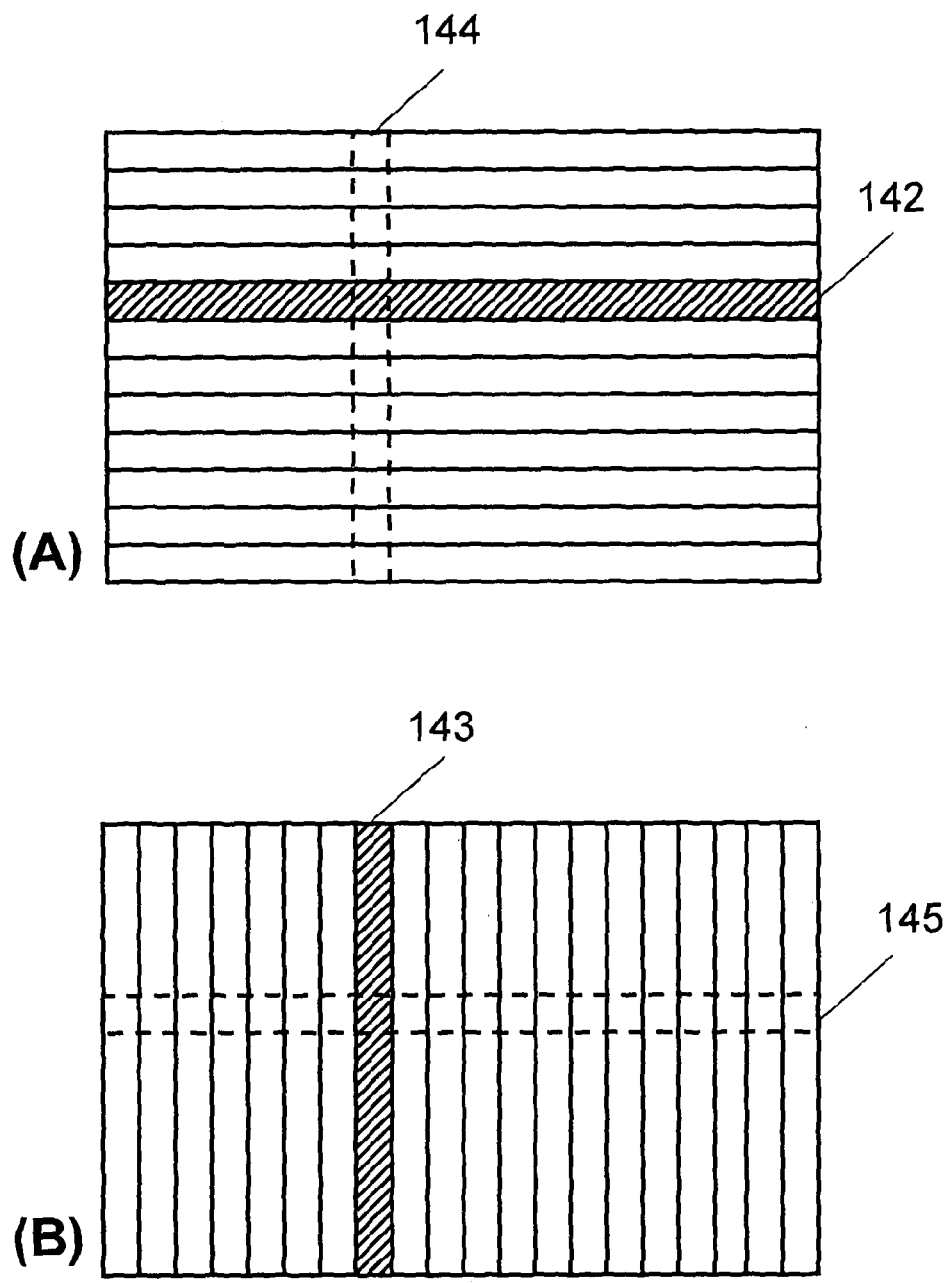
FIG. 12A is a schematic plan view illustrating a first aspect of the localization of an eye feature by a two layer imaging grating each layer comprising elongate elements with the elements of the two gratings at right angle.
FIG. 12B is a schematic plan view illustrating a second aspect of the localization of an eye feature by a two layer imaging grating each layer comprising elongate elements with the elements of the two gratings at right angle.

FIG. 12 shows how the first and second SBG lens arrays of FIGS. 7-10 may be used to localize an eye feature such as speckle by scanning row and column SBG elements such as 142 and 143.

Figure 13:
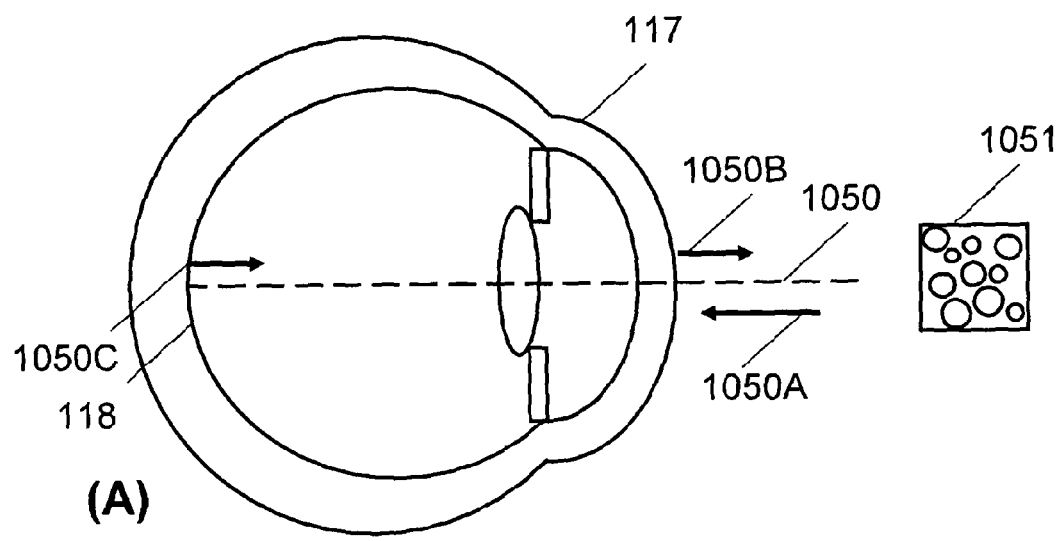
FIG. 13A is a schematic cross of the human eye in a first rotational state showing a typical speckle pattern formed by the cornea and retina.
FIG. 13B is a schematic cross of the human eye in a first rotational state showing a typical speckle pattern formed by the cornea and retina.
Figure 13:
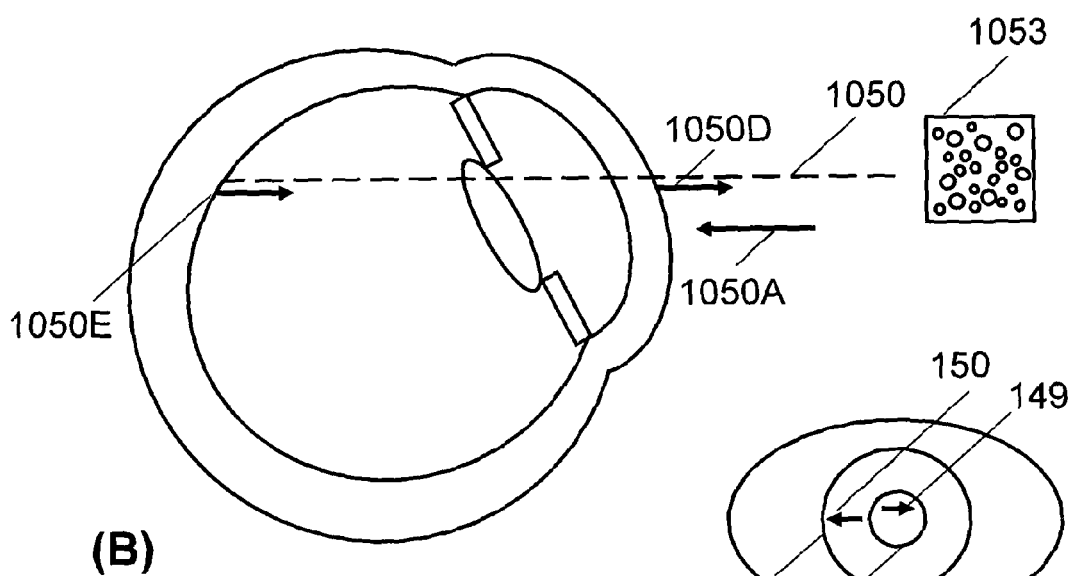

FIG. 13 illustrates how the size of speckle feature as recorded in two captured speckle images may vary with the eye orientation and displacement with respect to the eye optical axis 1050. FIG. 13A illustrates speckle formed by illuminating the eye along the direction 1050A which is initially parallel to the eye optical axis. The components of the corneal and retinal speckle light parallel to the eye optical axis are indicated by 1050B,1050C. FIG. 14A shows the formation of speckle with the eye rotated in the plane of the drawing. The detected corneal and retinal speckle light 1050D,1050E parallel to the direction 1050 which is now no longer parallel to the eye optical axis is shown. As shown by the insets 1051,1053 the size and spatial distribution of the speckles changes as the eye rotates. Correlation of the two speckle patterns will provide a measure of the eye rotation. Note that, typically, the speckle patterns recorded at the detector will combine separate speckle patterns from the cornea and retina as well as other surfaces and biological media interacting with the illumination beam.

Figure 14:
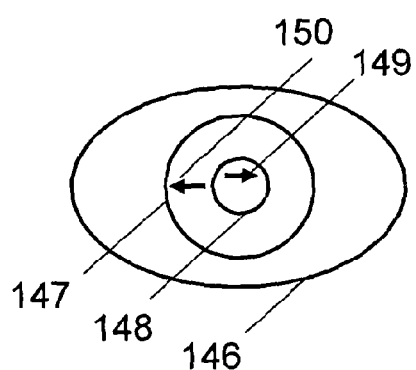
FIG. 14 is a schematic front elevation view of a human eye show showing the directions of motions of speckle patterns produced by the retina and cornea.
Figure 15:
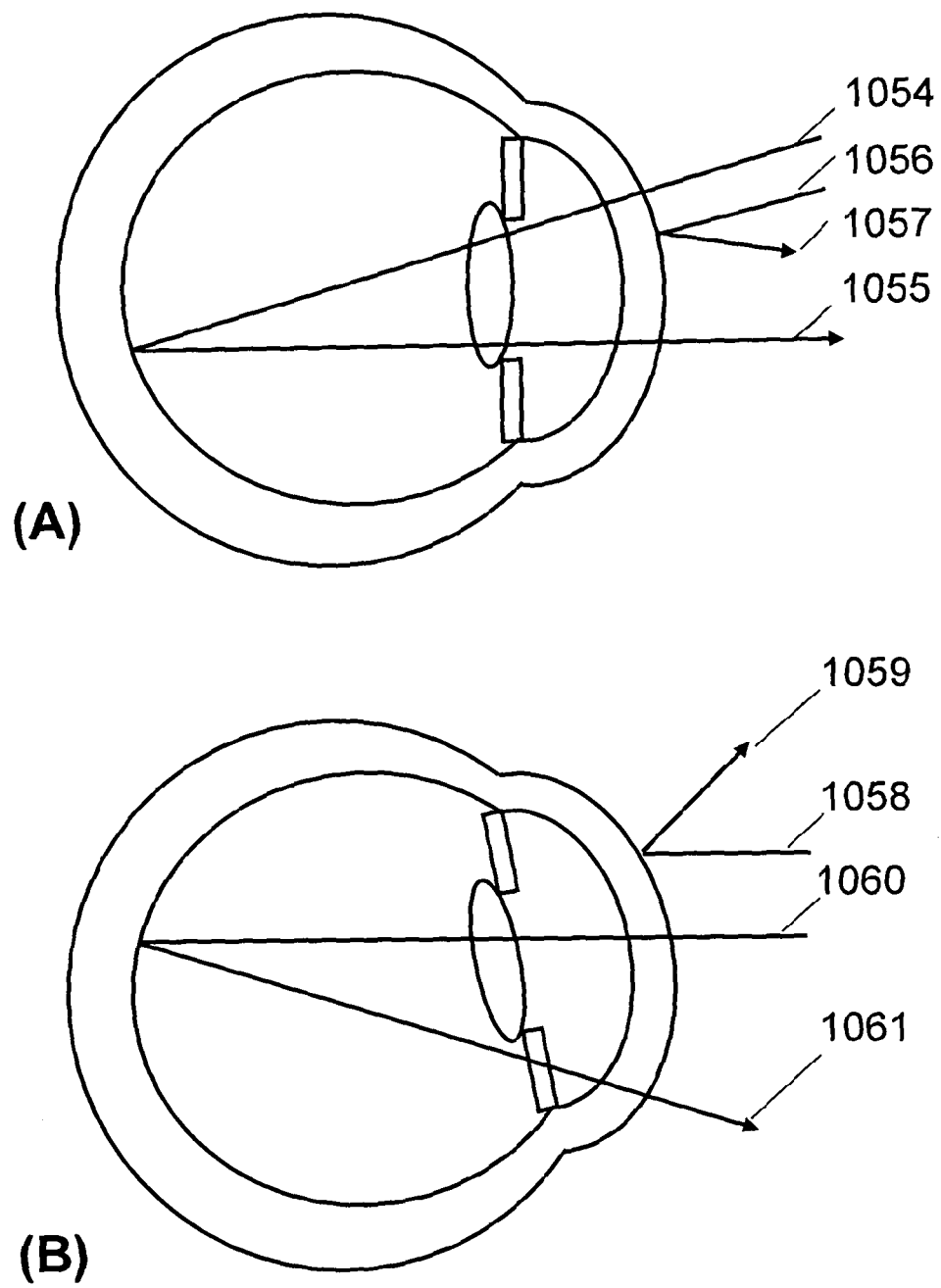
FIG. 15A is a schematic cross section view of a human eye in a first rotational state showing reflection from the retina and cornea.
FIG. 15B is a schematic cross section view of a human eye in a second rotational state showing reflection from the retina and cornea.

In one embodiment of the invention the eye tracker processor compares the speckle images due to light being scattered from the retina and cornea. When the eye is panned horizontally or vertically the relative position of the speckle pattern from the cornea and retina change accordingly allowing the direction of gaze to be determined from the relative trajectories of the reflected light beams. FIG. 14 represents the front of the eye 146 cornea 147 and illuminated region 148 of the retina illustrates the direction of movement of corneal and retinal speckle features as indicated by the vectors 149,150 correspond to the ocular displaces illustrated in FIG. 15. FIG. 15A represents the reflection of rays from the cornea 1056,1057 and retina 1054,1055 for one eye position. FIG. 15B shows the reflection paths from the cornea 1058,1059 and the retina 1060, 1061 after a horizontal (or vertical) eye rotation.

Figure 16:
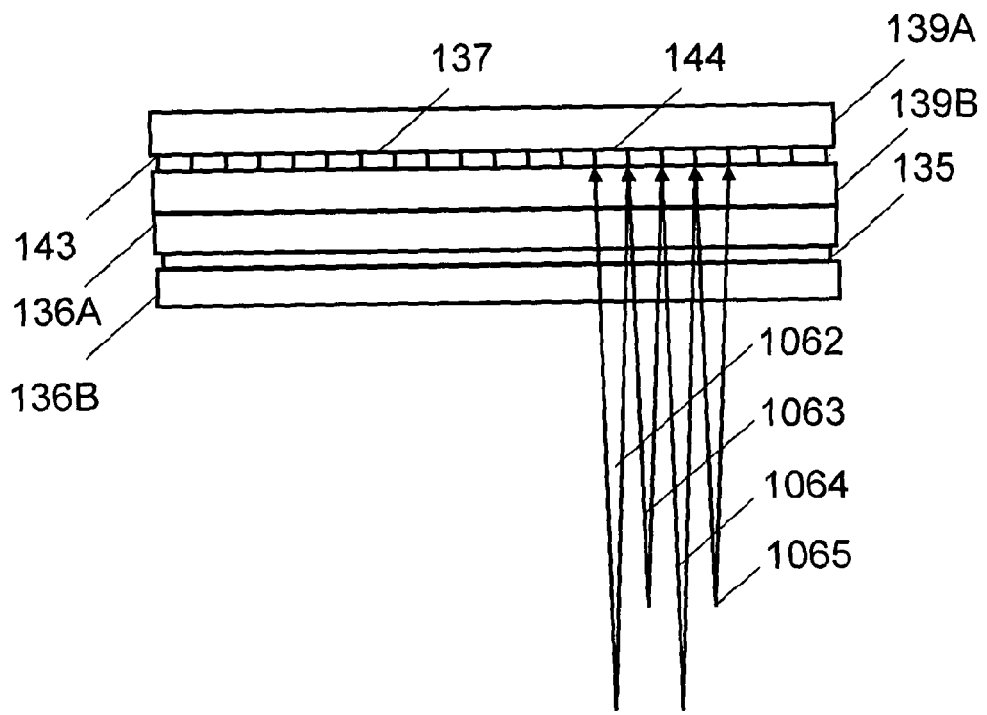
FIG. 16 is a schematic cross section view of an imaging grating comprising an array of SBG lens elements with focal length varying across the exit pupil in one embodiment of the invention.
Figure 17:
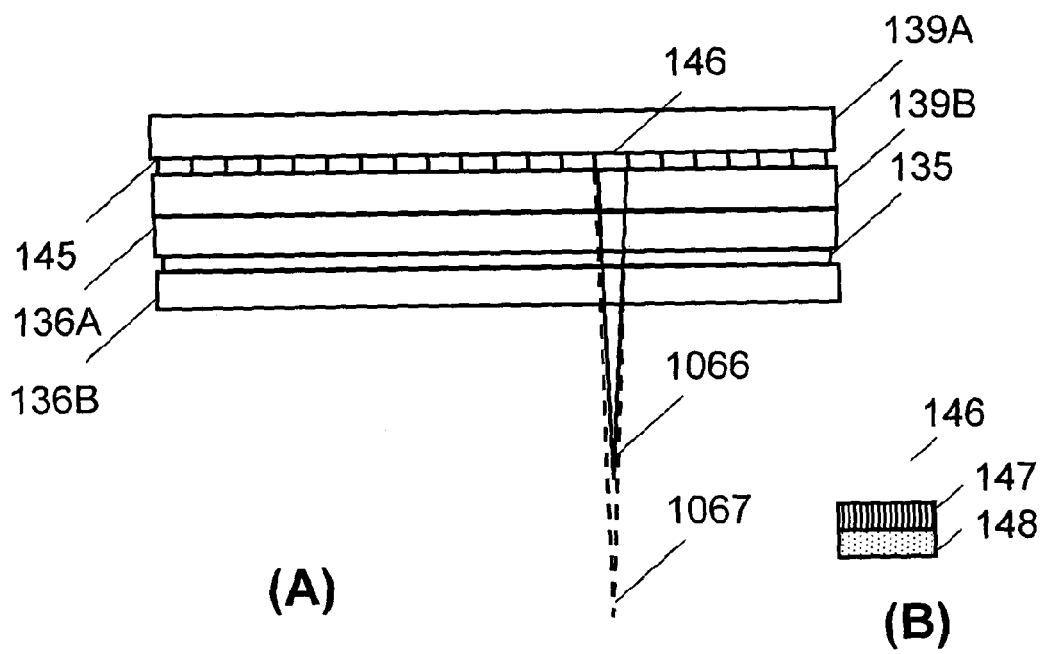
FIG. 17A is a schematic cross section view of an imaging grating comprising an array of variable power lenses in one embodiment of the invention.
FIG. 17B is a detail of FIG. 17A showing a variable power lens comprising a variable index layer and a diffractive element of fixed focal length.

In one embodiment of the invention based on the one of FIGS. 7-10 the imaging grating comprises an SBG array 143 in which the lens elements 144 have varying focal length across the exit pupil. In the embodiment of FIG. 16 grating elements of first and second focal length indicated by the divergent beams 1062,1064 and 1063,1065 are uniformly interspersed. In one embodiment of the invention illustrated in FIG. 17A the imaging waveguide comprises arrays 145 of variable power lens elements 146. As shown in the detail of FIG. 17B a variable power lens would be provided by combining a diffractive element 147 of fixed focal length with a variable index layer 148.

Figure 18:
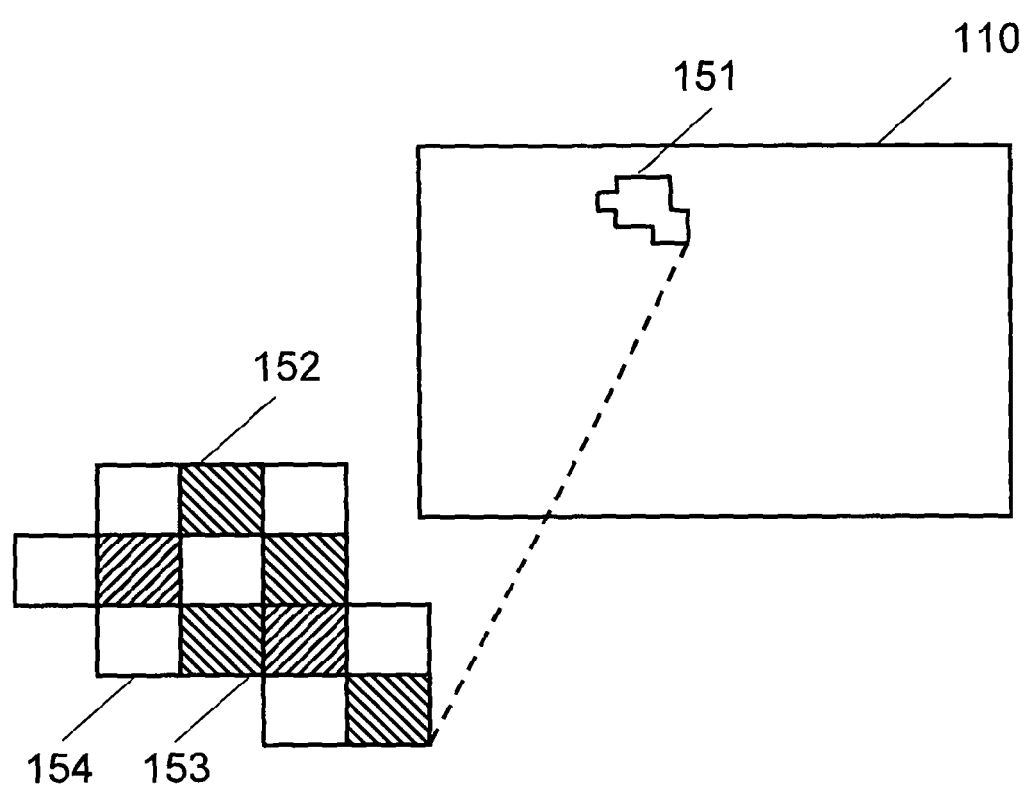
FIG. 18 is a schematic illustrate of an imaging grating in one embodiment of the invention in which the imaging grating comprises an array of interspersed grating elements having at least two different prescriptions.

In one embodiment of the invention shown in the schematic view of FIG. 18 the imaging grating comprises a single layer two dimensional SBG array. A group of elements labelled 152 which comprises interspersed elements such as 153,154. The group forms the image region 151 at the detector 110. Each SBG element is characterised by one from a set of at least two different prescriptions. FIG. 18 does not show the details of the waveguide and the illumination and input/output gratings. At least one of the SBG prescriptions corresponds to a lens for forming an image of the eye on the detector. At least one prescription is optimised for imaging a speckle pattern formed by a surface of the eye. Hence the embodiment of FIG. 18 allows eye tracking to be performed using speckle patterns and conventional features such as Purkinje reflections.

An Embodiment Using Separate Illumination and Detection Gratings

Figure 19:
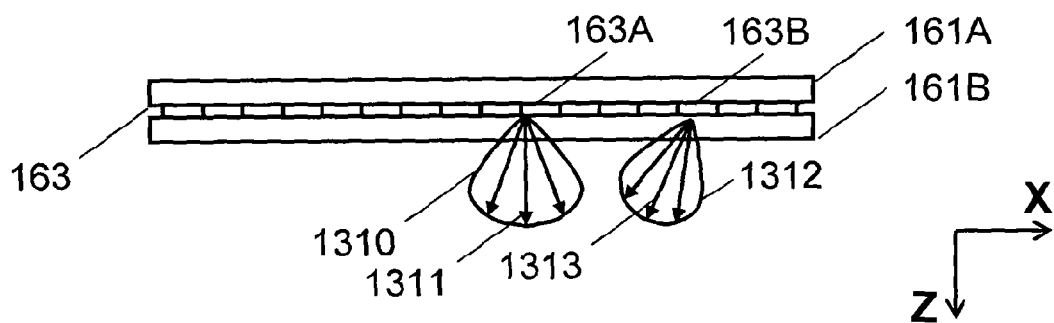
FIG. 19 is a schematic cross section view of the illumination grating of an eye tracker using separate illumination and imaging gratings in one embodiment of the invention.
Figure 20:
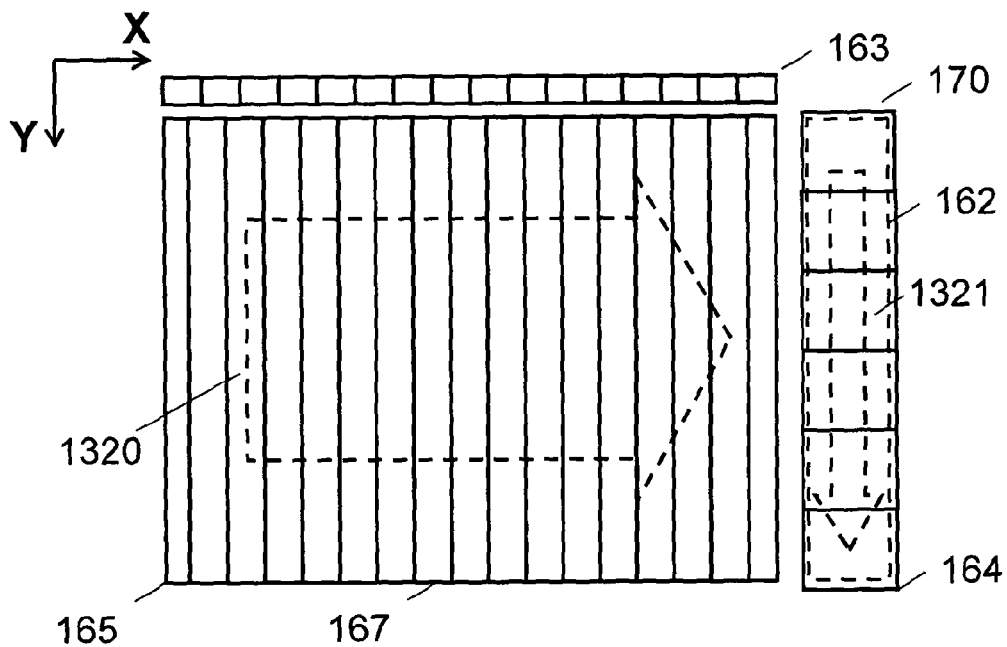
FIG. 20 is a schematic plan view the illumination grating of an eye tracker using separate illumination and imaging gratings in one embodiment of the invention.
Figure 21:
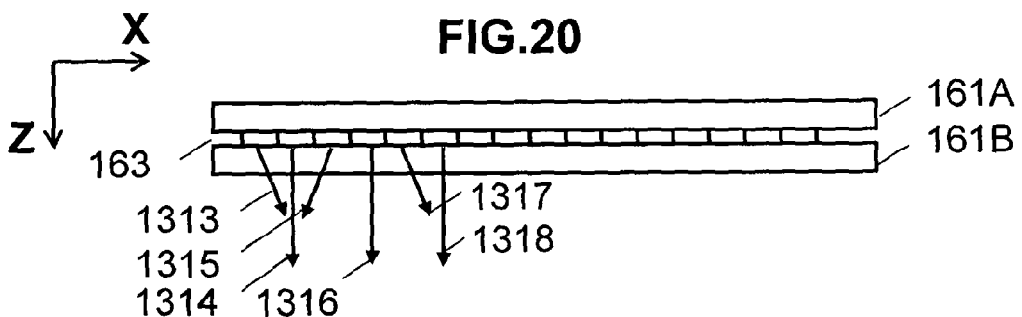
FIG. 21 is a schematic cross section view of an alternative illumination grating of an eye tracker using separate illumination and imaging gratings in one embodiment of the invention.
Figure 22:
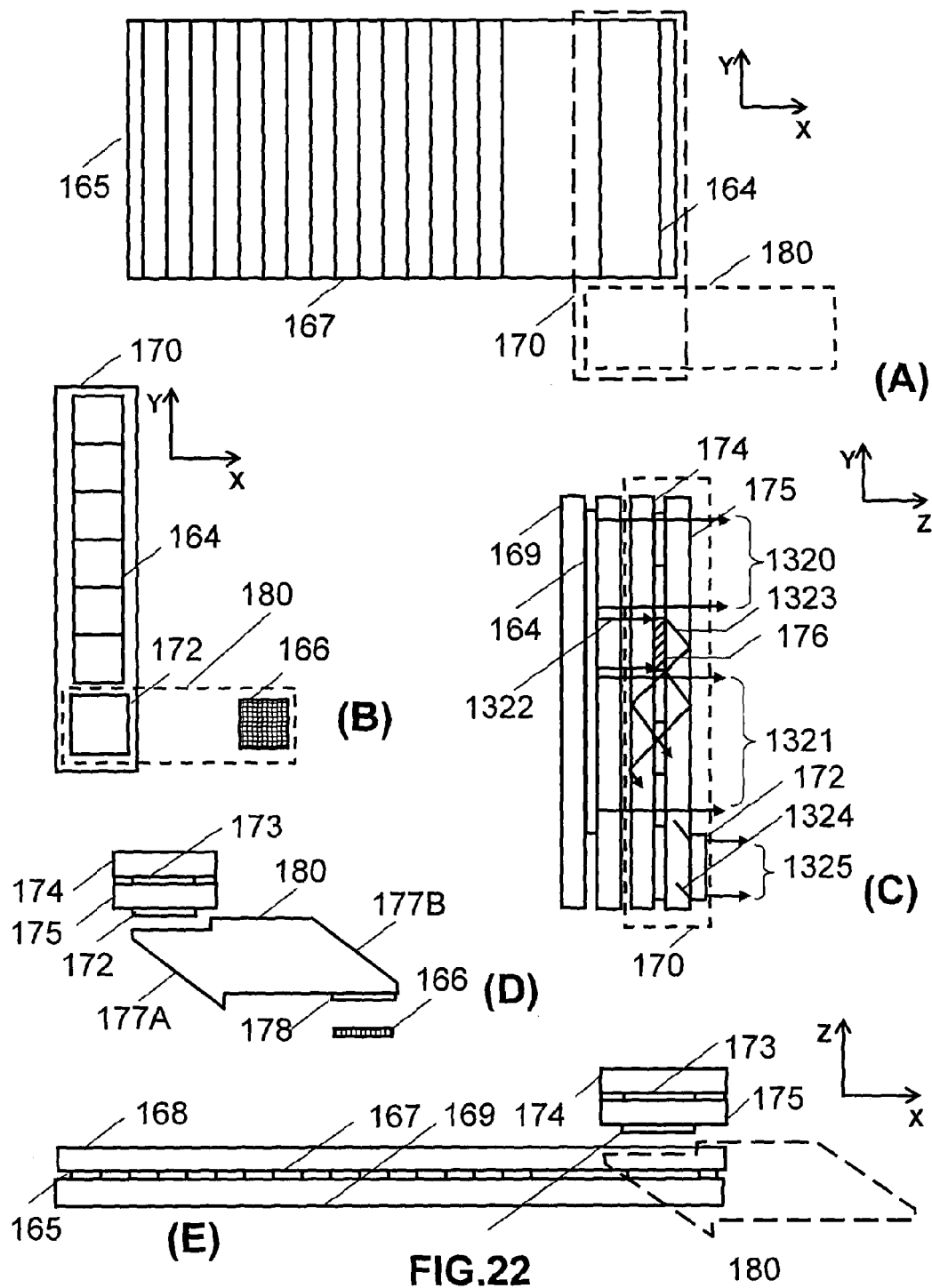
FIG. 22A is a schematic plan view of the imaging grating, the image sampling grating and the detector module of an eye tracker using separate illumination and imaging gratings in one embodiment of the invention.
FIG. 22B is a schematic plan view of image sampling grating and the detector module of an eye tracker using separate illumination and imaging gratings in one embodiment of the invention.
FIG. 22C is a schematic cross section view of the imaging grating and the image sampling grating of an eye tracker using separate illumination and imaging gratings in one embodiment of the invention.
FIG. 22D is a schematic cross section view of image sampling grating and the detector module of an eye tracker using separate illumination and imaging gratings in one embodiment of the invention.
FIG. 22E is a schematic cross section view of the imaging grating, the image sampling grating and the detector module of an eye tracker using separate illumination and imaging gratings in one embodiment of the invention.

FIGS. 19-24 provide schematic illustrations of aspects of an eye tracker based on the principles of FIGS. 1-6. In this embodiment of the invention the earlier described imaging, illumination, input and output gratings are augmented by an additional grating to be referred to as an image sampling grating which overlays the output grating. FIG. 19 shows a side elevation view of the illumination grating 163. FIG. 20 is a plan view showing the imaging grating 165, the illumination grating 163 and the image sampling grating 170 overlaid on the output grating 164. FIG. 21 is a side elevation view of an alternative embodiment of the illumination grating 163. FIG. 22A is a plan view of the imaging grating, the image sampling grating 14 and the detector module 180. FIG. 22B is a plan view of the image sampling grating and the detector module. FIG. 22C is a cross sectional view showing the imaging grating and the image sampling grating. FIG. 22D is a cross sectional view of the image sampling grating and the detector module. Finally, FIG. 22E is a cross sectional view of the imaging grating, the image sampling grating and the detector module. To assist the reader the projection plane of each illustration is referred to a Cartesian XYZ reference frame.

The imaging grating 165 comprises an array of column-shaped SBG elements, such as the one labelled 167, sandwiched by substrates 168,169. Column elements of the imaging grating 165 are switched on and off in scrolling fashion backwards and forward along the direction indicated by the block arrow 1320 in FIG. 20 such that only one SBG column is in its diffractive state at any time.

The illuminator array 163 is shown in detail in FIG. 19 comprises substrates 161A,161B sandwiching an array of SBG rectangular elements such as 163A,163B. The SBG elements may have identical diffracting characteristics or, as shown in FIG. 19, may have characteristics that vary with position along the array. For example, the element 163A provides a diffusion distribution 1310 centred on a vector at ninety degrees to the array containing rays such as 1311. However, the element 63B provides an angled distribution 1312 containing rays such as 1313. In an alternative embodiment shown in FIG. 21 the diffusion polar distributions may have central ray directions that varying in a cyclic fashion across the array as indicated by the rays 1313-1318.

The image sampling grating 170, comprising an array of rectangular SBG beam deflecting elements 173 such as 176 (shown in its diffracting state in FIG. 22C) sandwiched by substrates 174,175. The waveguide containing the imaging grating 165, illumination grating 163 and the output grating 164 is separated from the image sampling grating 170 by a medium (not illustrated) which may be air or a low refractive index transparent material such as a nanoporous material.

Infrared light from a surface of the eye is coupled into the waveguide by an active imaging grating element, that is, by a diffracting SBG column. The guided beam undergoes TIR in the waveguide up to the output grating. As shown in FIG. 22C the output grating 164 deflects the beam through ninety degrees into the direction 1322 towards the image sampling grating 170. As shown in FIG. 22C a portion of the beam 1322 is deflected into the image sampling grating by an active SBG element 176 where it undergoes TIR in the direction indicated by the ray 1323 (and also by block arrow 1321 in FIG. 20). The light that is not sampled by the image sampling grating indicated by 1320 1321 is trapped by a suitable absorbing material, which is not illustrated. The TIR beam is deflected in the detector module 180 by a first holographic lens 172 to provide out image light 1325. Turning now to FIG. 22D we see that the detector module contains mirror surfaces 177A,177B and a further holographic lens 178 which forms an image of the eye features or speckle pattern that is being tracked on the detector array 166. Note the holographic lens 172,178 may be replaced by equivalent diffractive elements based on Bragg or surfaces relief gratings. Conventional refractive lens elements may also be used where size constraints permit.

Figure 23:
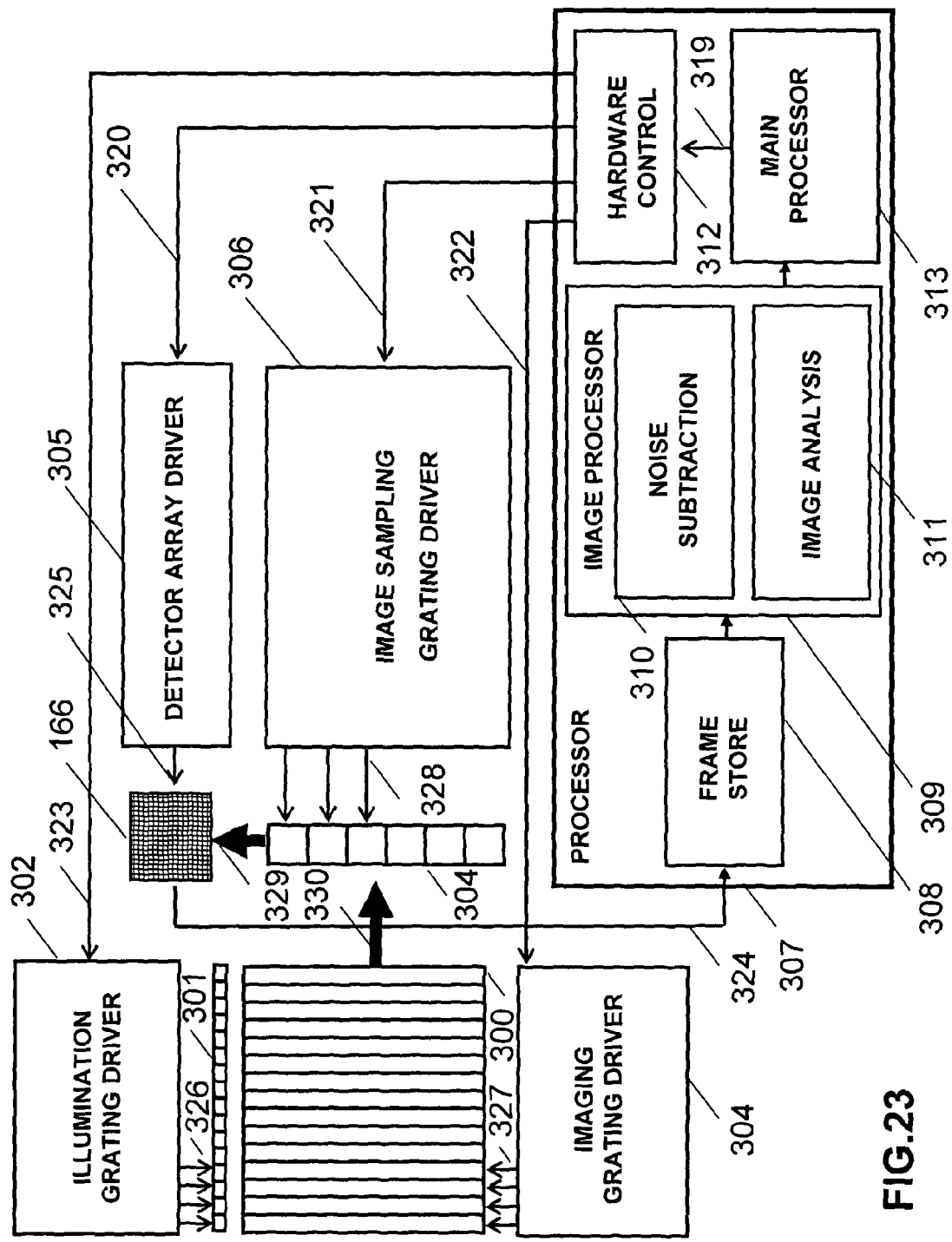
FIG. 23 is a block diagram showing the principal modules of an eye tracker system using separate illumination and imaging gratings in one embodiment of the invention.

FIG. 23 provides a system block diagram of the eye tracker of FIGS. 19-22. The system modules comprise the imaging grating 300, illumination grating 301, illumination grating driver 302, illumination sampling grating 303, imaging grating driver 304, detector driver 30, image sampling array driver 306, detector 166 and processor 307. The apparatus will also comprises a laser driver which is not illustrated. The optical links from the image grating to the image sampling array and the image sampling array to the detector are indicated by the block arrows 329,330. The processor 307 comprises a frame store 308 or other image memory device for the storage of captured eye image or speckle pattern frames and an image processor 309 further comprising hardware or software modules for noise subtraction 310 and image analysis 311. The processor further comprises hardware control module 312 for controlling the illumination, imaging and image sampling grating drivers, all said modules operating under the control of a main processor 313. Data and control links between components of the system are indicated by 319-325. In particular, each driver module contains switching circuitry schematically indicated by 326-328 for switching the SBG elements in the imaging grating, illumination grating array, and image sampling grating.

Figure 24:
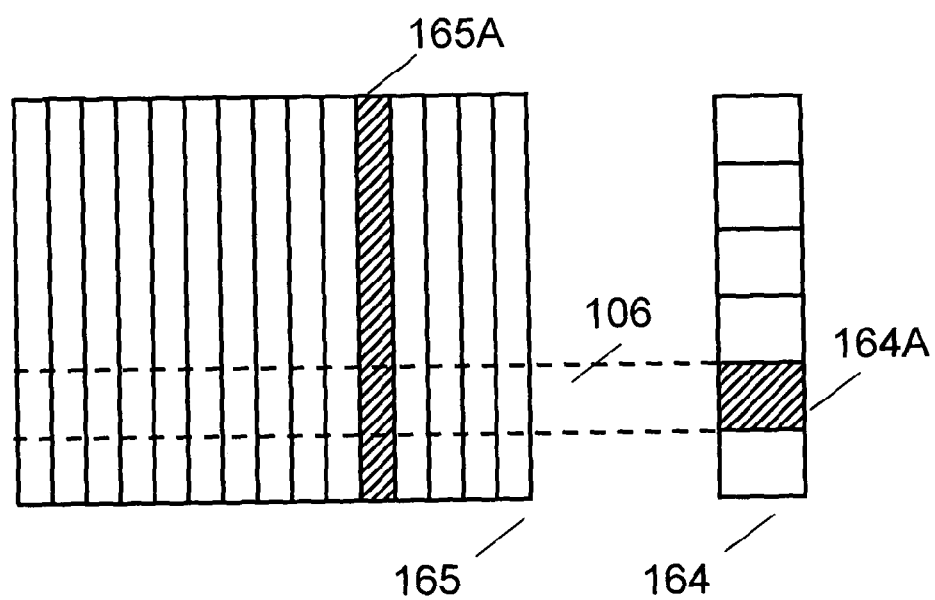
FIG. 24 is a schematic illustration of a grating element switching scheme provided by the imaging grating and image sampling grating in one embodiment of the invention.

FIG. 24 illustrates the switching scheme used in the imaging grating and image sampling grating. The illumination grating elements are switched in phase with the imaging grating columns. Column element 165A of the imaging grating array 165 and element 170A of the readout array 170 are in their diffracting states. The projection (indicated by 170B) of element 170A on the column 65A defines an active detection aperture. Using such as scheme it is possible to track features of the eye using a X,Y localisation algorithm aided by predictions obtained from analysis of displacement vectors determined from successive frames.

An Embodiment Using a Common Illumination and Detection Grating

Figure 25:
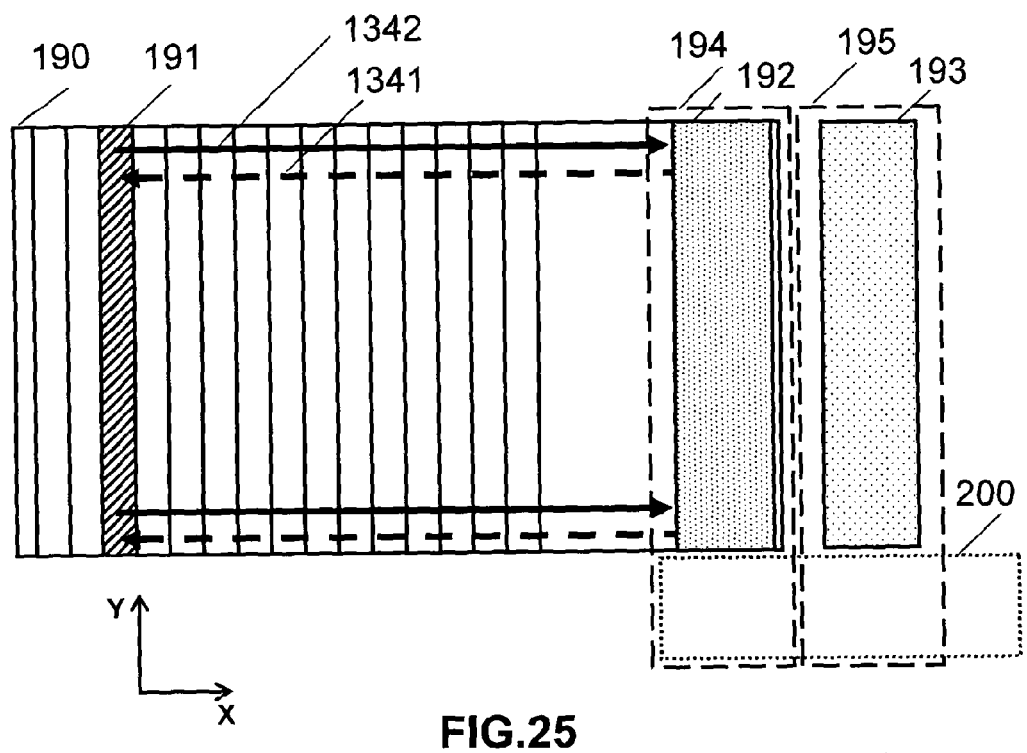
FIG. 25 is a schematic plan view of an eye tracker using common illumination and imaging gratings in one embodiment of the invention.
Figure 26:
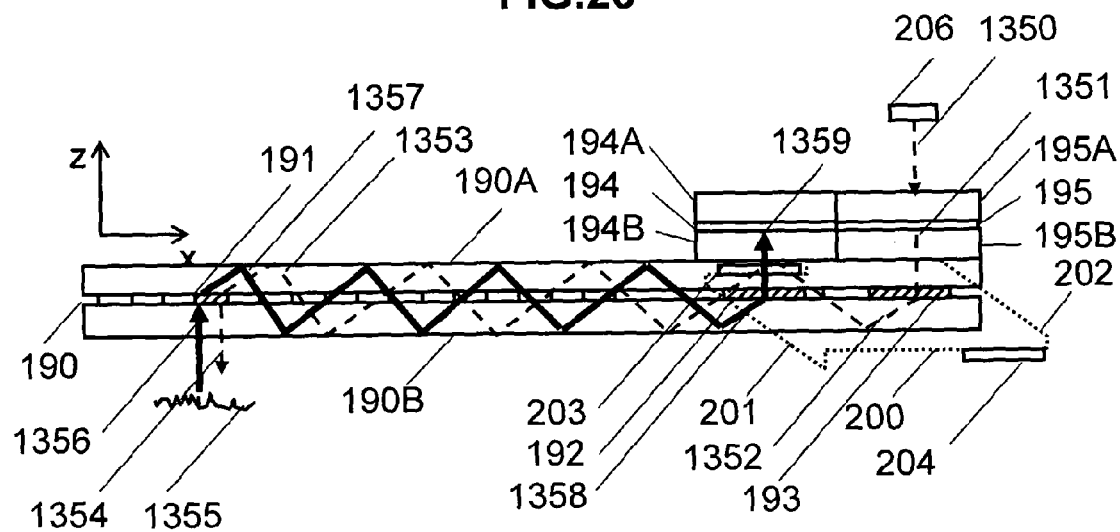
FIG. 26 is a schematic cross section view showing the imaging and illumination grating and the input, output, image sampling and detector sampling gratings of an eye tracker using common illumination and imaging gratings in one embodiment of the invention.
Figure 27:
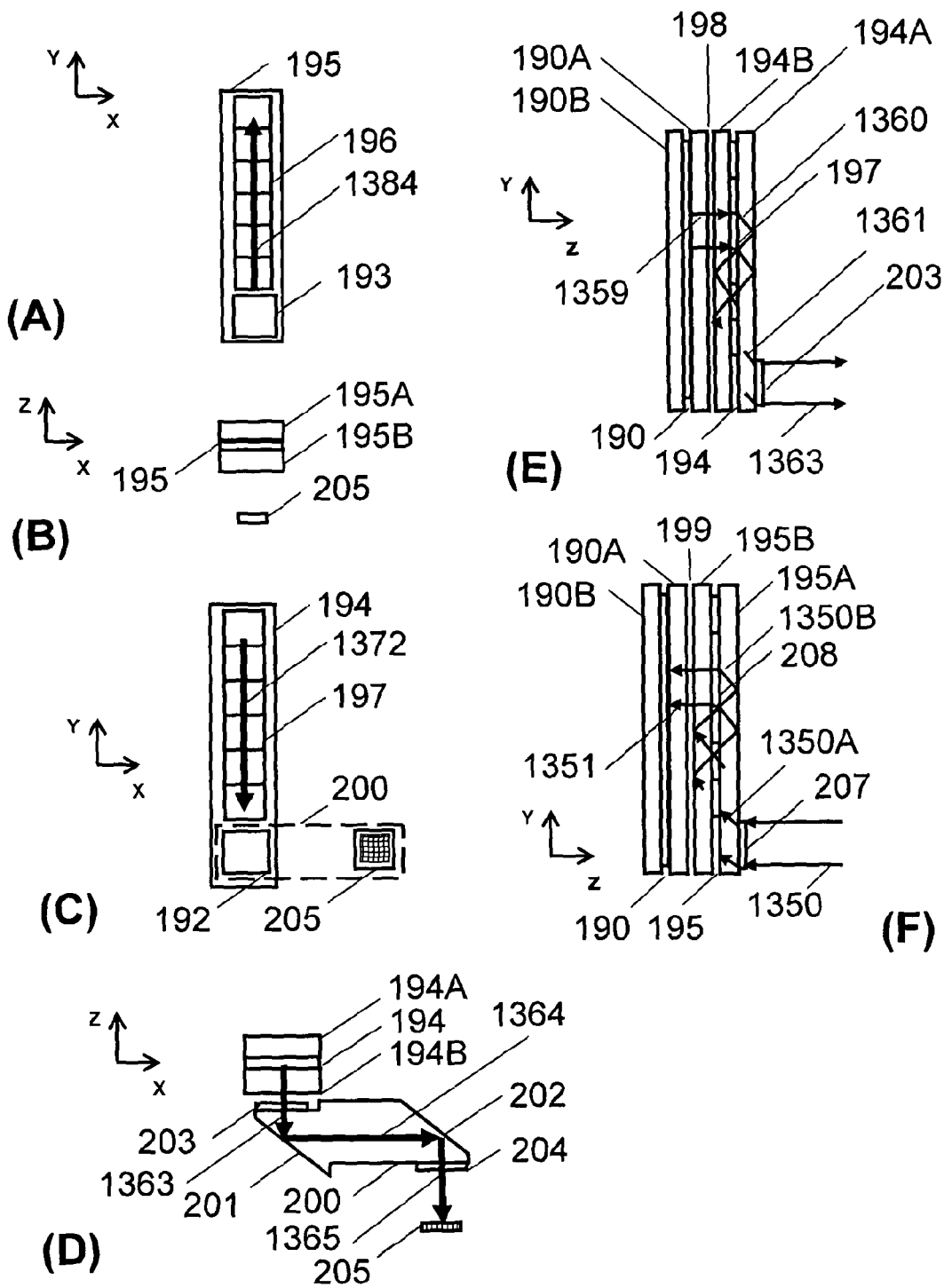
FIG. 27A is a schematic plan view of the image sampling grating of an eye tracker using common illumination and imaging gratings in one embodiment of the invention.
FIG. 27B is a schematic cross section view of the illumination sampling grating, the input grating and laser of an eye tracker using common illumination and imaging gratings in one embodiment of the invention.
FIG. 27C is a schematic plan view image sampling grating and the detector module with detector overlaid of an eye tracker using common illumination and imaging gratings in one embodiment of the invention.
FIG. 27D is a schematic plan side elevation view showing the image sampling grating and detector of an eye tracker using common illumination and imaging gratings in one embodiment of the invention.
FIG. 27E is a schematic cross section view of the output grating and the image sampling grating an eye tracker using common illumination and imaging gratings in one embodiment of the invention.
FIG. 27F is a schematic cross section view of the input grating and the illumination sampling of an eye tracker using common illumination and imaging gratings in one embodiment of the invention.

FIGS. 25-27 provide schematic illustrations of aspects of an eye tracker that extends the embodiment of FIGS. 19-24 by introducing a further grating component to be referred to as an illumination sampling grating which overlays the input grating. The other feature of this embodiment is that the illumination grating is no longer separate from the imaging gratings. Instead the two are combined such that a common column grating area is used to illuminate and image the eye with the illumination and image wave guided light propagating in opposing directions. The combined gratings will be referred to as the illumination and imaging grating. As will be explained below the function of the illumination sampling grating, which is similar in structure to the image sampling grating, is to concentrate the available illumination into region of the eye selected by the image sampling grating. This provides the dual benefits of light efficiency and avoidance of stray light from regions of the eye that are not being tracked. Turning to the drawings FIG. 25 is a plan view showing the imaging and illumination grating 190, the image sampling grating 194, illumination sampling grating 195 the input grating 193 and output grating 192 and the detector module 200. Column elements of the illumination and imaging grating are switched on and off in scrolling fashion backwards and forward such that only one SBG column is in its diffractive state at any time. The counter propagating beam paths are indicated by 1341,1342.

FIG. 26 shows the components of FIG. 25 in a side elevation view.

FIG. 27A is a plan view of the illumination sampling grating

FIG. 27B is a cross sectional view of the illumination sampling grating 195 including the input grating 193 and the laser 205.

FIG. 27C is a plan view of the image sampling grating 194 showing the detector module 200 and detector 205 overlaid.

FIG. 27D is a side elevation view showing detector module 200 in more detail. The detector 205 and a cross section of the image sampling grating 194 are included.

FIG. 27E is a cross sectional view of the output grating 192 and the image sampling grating 194.

FIG. 27F is a cross section view of the input grating 193 and the illumination sampling grating 194.

To assist the reader the projection plane of each illustration is referred to a Cartesian XYZ reference frame.

The illumination and imaging grating comprises the array 190 of column-shaped SBG elements, such as the one labelled 191 sandwiched by the transparent substrates 190A, 190B. The input and output grating which are disposed in the same layer are labelled by 193,192 respectively. The detector module 200 is delineated by a dotted line in FIGS. 25-26 and in more detail in FIG. 27D.

The image sampling grating 194, comprises an array of rectangular SBG beam deflecting elements (such as 197) sandwiched by substrates 194A,194B. Typically the imaging grating and image sampling grating are separated by a medium 198 which may be air or a low refractive index transparent material such as a nanoporous material.

The illumination sampling grating 195 which is has a very similar architecture to the image sampling grating comprises an array of rectangular SBG beam deflecting elements (such as 196) sandwiched by substrates 195A,195B. Typically the imaging grating and image sampling grating are separated by a medium 199 which may be air or a low refractive index transparent material such as a nanoporous material.

Referring to FIG. 26 and FIG. 27F illumination light 1350 from the laser is directed into the illumination sampling grating by a coupling grating 207. The light then proceeds along a TIR path as indicated by 1350A, 1350B up to an active element 208 where it is diffracted into the direction 1351 towards the input grating. Not that the image sampling grating directs all of the illumination light through the active element of the illumination sampling grating the elements of which are switched in synchronism with the elements of the image sampling grating to ensure that at any time the only the region of the that is being imaged receives illumination. The illumination path in the waveguide is indicated by 1352-1354.

Infrared light 1356 (also illustrated as the speckle pattern 1355) from a surface of the eye is coupled into the waveguide by a diffracting SBG column such as 191. The guided beam indicated by 1357,1358 undergoes TIR in the waveguide up to the output grating 192. The output grating deflects the beam through ninety degree into the direction 1359 towards the image sampling grating. As shown in FIG. 27E the beam in direction 1359 is deflected into the image sampling grating by an active SBG element 197 where it undergoes TIR along the ray path indicated by 1360, 1361. The TIR beam is deflected into the detector module 200 as light 1363 by a first holographic lens 203. Any light that is not sampled by the image sampling grating is trapped by a suitable absorbing material, which is not illustrated.

The detector module contains mirror surfaces 201,202 and a further holographic lens 204 which forms an image of the eye features or speckle pattern that is being tracked on the detector array 205. The ray path from the image sampling grating to the detector is indicated by the rays 1363-1365. Note the holographic lens 203,204 may be replaced by equivalent diffractive elements based on Bragg or surfaces relief gratings. Conventional refractive lens elements may also be used where size constraints permit.

In one embodiment of the invention illumination light from laser module is converted into S polarized light which is coupled into the eye tracker waveguide by the input grating. This light is then converted into circularly polarized light using a quarter wave plate. An active SBG column will then diffract the P-component of the circularly polarized wave guided light towards the eye, the remaining P-polarized light being collected in a light trap. The P-polarized light reflected back from the eye (which will be substantially P-polarized) is then diffracted into a return TIR path by the active SBG column and proceeds to the detector module as described above. This scheme ensures that image and illumination light is not inadvertently coupled into the input and output gratings respectively. In other embodiments of the invention the unwanted coupling of the image and illumination light may be overcome by optimizing the TIR angles, the angular bandwidths of the imaging and illumination gratings, the spacings along the waveguide of the input and output gratings, and the illumination and imaging beam cross sections. In one embodiment the illumination light which will typically in most embodiments of the invention be collimated may be angled such that the waveguide propagation angle of the illumination beam differs from the waveguide angles of the image light.

An important feature of the invention is that elements of the illumination sampling grating are switched to allow illumination to be localized to a small region within the active column of the DigiLens ensuring that the illumination is concentrated exactly where it is needed. This also avoids stray light reflections a problem which can consume significant image processing resources in conventional eye tracker designs.

Since the illumination is scrolled the cornea and retina are not exposed to continuous IR exposure allowing higher exposures levels to be used leading to higher SNR. A safety interlock which is not illustrated may be included to switch off the laser when no tracking activity has been detected for a predefined time.

The proposed scheme for switching the columns and readout elements in the embodiments of FIGS. 25-27 is based on tracking the movement of the pupil using a X,Y localisation algorithm similar to the one illustrated in FIG. 24 which shows the how the ith activation column DigiLens and jth activated element of the Readout Array are used to select the speckle pattern region (X,Y).

The detected speckle pattern (or other eye signature) is stored and compared with other saved patterns to determine the eye gaze trajectory and to make absolute determinations of the gaze direction (bore sighting). Initial calibration (that is, building up the database of saved patterns) is carried out by directing the user to look at test targets at predefined points in the FOV. As discussed above the eye tracker tracks eye movements by measuring the spatio-dynamic characteristics of speckle patterns projected off the cornea and retina. Speckle detection avoids the image analysis problems of identifying and tracking recognisable features of the eye that are encountered in Purkinje imaging schemes. Instead we detect and correlate speckle patterns (or other eye signatures) using a spatio-temporal statistical analysis. A prerequisite is achieving an adequate level of speckle contrast after detector noise and ambient light have been subtracted from the detected signal and being able to resolve speckle grains.

Figure 28:
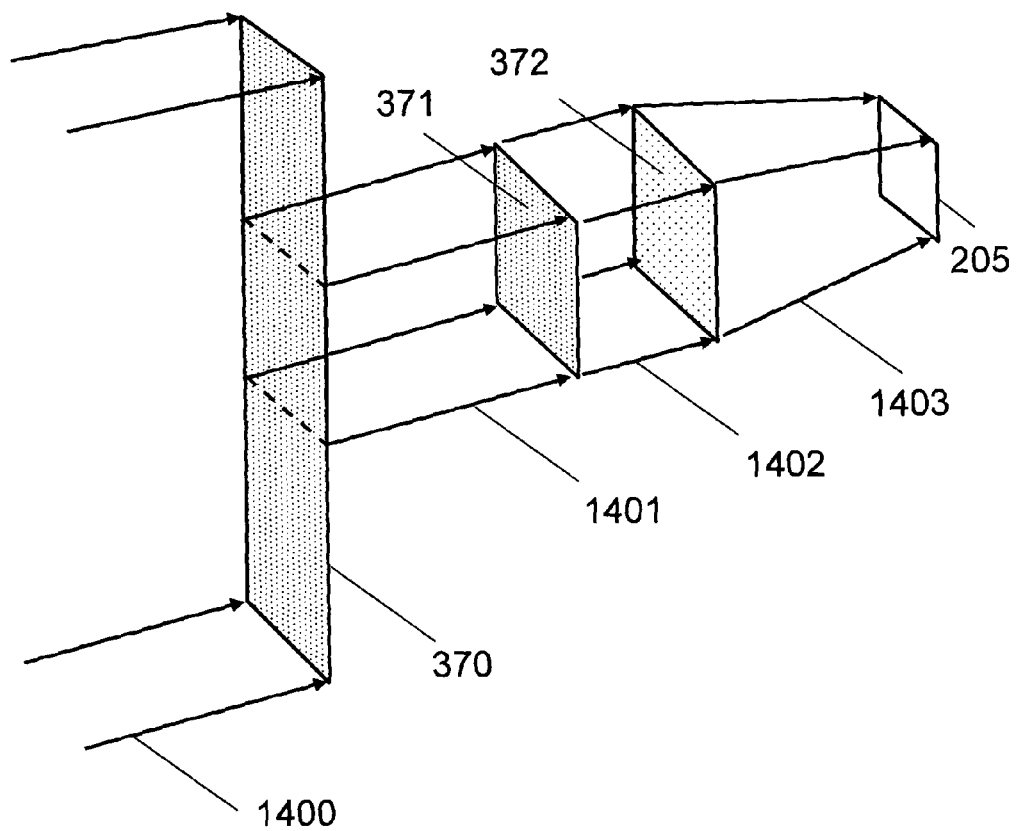
FIG. 28 is a simplified representation of the imaging process an eye tracker using common illumination and imaging gratings in one embodiment of the invention.

FIG. 28 is a simplified representation of the detection path starting with the collimated rays 1400 from an active column element 370 of the imaging array. The rays 1400 are sampled by an element 371 of the detector grating to provide the rays 1402 which are imaged by the holographic lens 372 to provide the rays 1403 incident on the detector 205.

Figure 29:
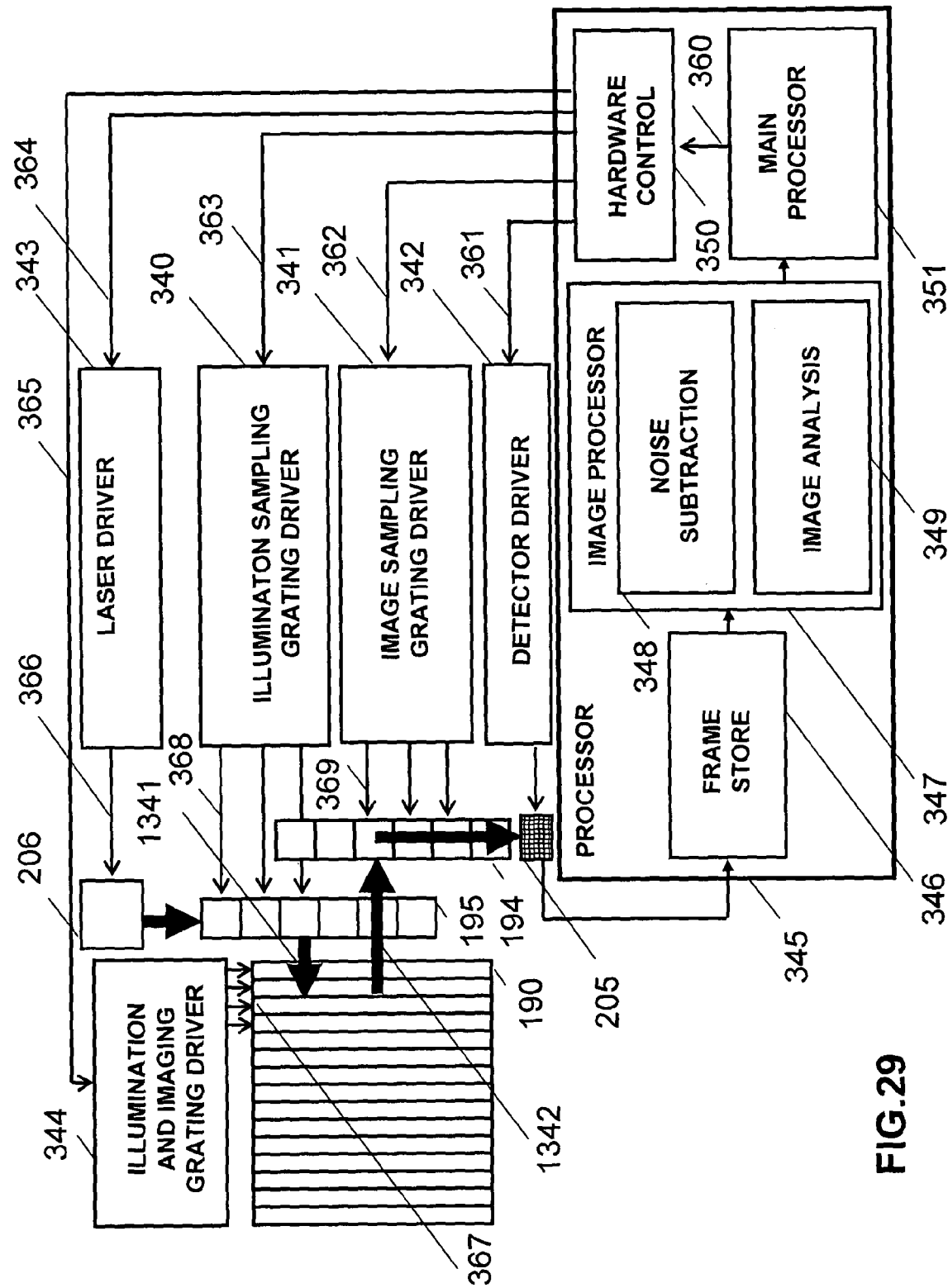
FIG. 29 provides a system block diagram showing the key modules of an eye tracker using common illumination and imaging gratings in one embodiment of the invention.

FIG. 29 provides a system block diagram of the eye tracker of FIGS. 26-27. The system modules comprise the illumination and imaging grating 190, image sampling grating 194, illumination sampling grating 195, detector 205, laser 206, illumination sampling array driver 340, image sampling array driver 341, detector driver 342, laser driver 343, illumination and imaging grating driver 344 and processor 345. The processor 345 comprises a frame store or other image storage media 346 for the storage of captured eye image or speckle pattern frames and an image processor 347 further comprising hardware or software modules for noise subtraction 348 and image analysis 349. The processor further comprises hardware control module 350 for controlling the illumination, imaging and image sampling grating drivers, all said modules operating under the control of a main processor 351. In one embodiment of the invention the detector array is a detector array of resolution 16×16 with a framing rate of 2300 fps of the type commonly used in infrared mouse equipment. The above described modules are connected by communication and control links schematically indicated by 360-369 include control lines for switching the SBG elements in the imaging grating, illumination sampling grating array, and image sampling grating 367-369.

Prerequisites for measuring eye displacement vectors (rotational and/or translational) include achieving an adequate level of speckle contrast (after detector noise and ambient light have been subtracted from the detected signal) and being able to resolve individual speckle grains. A high signal to noise ratio (SNR) is essential for detecting variations in speckle properties at required angular resolution. The SNR depends on the speckle contrast, which is defined as the ratio of the root means square (rms) variation of the speckle intensity to the mean intensity. The speckle contrast lies between 0-1 assuming Gaussian statistics. The detector should have low noise and a short integration time. If the motion of the eye is appreciably faster than the exposure time of the CCD camera rapid intensity fluctuations of the speckle pattern will occur, the average of the detected patterns resulting in a blurred image with reduced speckle contrast.

The smallest speckle size is set by the diffraction limit. Applying the well known formula from diffraction theory: $w=\sim 2.44\, D/a$ (assuming: a detector lens to detector distance $D\sim 70$ mm.; IR wavelength $\lambda=785$ nm.; and detector lens aperture $a\sim 3$ mm.) we obtain a diffraction limited speckle diameter w at the detector of ~64 microns. The resolution of a typical mouse sensor is around 400-800 counts per inch (cpi), with rates of motion up to 14 inches per second (fps). Hence the limiting speckle size is equivalent to one count per 64 micron at 400 cpi which is roughly compatible with the expected speckle size.

Ideally the eye tracker should be capable of tracking the eye's gaze direction everywhere within the eye box and for the full range of eye rotations. For the most demanding applications the design goal is to resolve 0.15° over the entire FOV. In the case of speckle trackers it is important to emphasize that we are not tracking ocular features in the conventional way. Instead we are measuring eye displacement vectors by comparing speckle patterns using statistical correlation techniques. As the eye translates and rotates within the eye box the DigiLens columns and readout elements select X-Y addressed speckle patterns (including corneal and retinal components) which are sequentially imaged onto a detector.

The processes of tracking and bore sighting are aided by recording large numbers of reference speckle pattern frames for different eye positions and orientations. Since the frames are of low resolution large numbers of samples may be collected without significant computational overhead.

The detector optical prescription will be determined by a detailed ray-tracing analysis and will require trade-offs of speckle size, F-number and DigiLens column width. The detector lens aperture defines the limiting speckle size. The detector field of view is determined by the detector size and the detector lens focal length. At present the preferred detector is the Agilent IR Mouse Sensor which uses a 16×16 element photo detector array.

In one embodiment the DigiLens provides 25 SBG scrolling columns×17 SBG readout elements. The Agilent device can be programmed to switch 2300 fps So a complete scan of the FOV will take (25×17)/2300 s.=185 ms. However, in practice the eye tracker will use a more sophisticated X-Y search process that localises the pupil using column and readout element coordinates. It is anticipated that on average around 10 search steps may be needed to converge on the pupil position resulting in a latency of 4.3 ms. On this basis the latency of the tracker is potentially ×100 lower than that of comparable image processing-based Purkinje-type eye trackers. It is also anticipated that the correlation process will be implemented in hardware resulting in a relatively modest data processing latency.

The proposed strategy for processing speckle data captured by the eye tracker is based on the following assumptions.
  a) Speckle patterns provide unique "fingerprints" of regions of the cornea and retina.
  b) Unlike speckle interferometry which requires that the speckle motion is less than speckle size, speckle imaging using a detector array requires that the speckle displacement from frame to frame is greater than the speckle size
  c) A displacement of the cornea and retina relative to the detector will result in a shift of the speckle pattern by the same amount
  d) The shifts of the corneal and retinal speckle patterns will be in opposite directions.
  e) The motion of the speckles can be determined from the correlation of two consecutive frame speckle patterns. This information together with the relative motion of the corneal and retinal speckle patterns can be used to determine eye displacement vectors.

f) The correlation and image analysis processes may take advantage standard techniques already developed in applications such as radar, biological imaging etc.

g) The speckle contrast and speckle size at the detector are compatible with the detector resolution and SNR.

h) An IR mouse detector such as the Agilent ADNS-2051 16×16 detector will be suitable.

Figure 30:
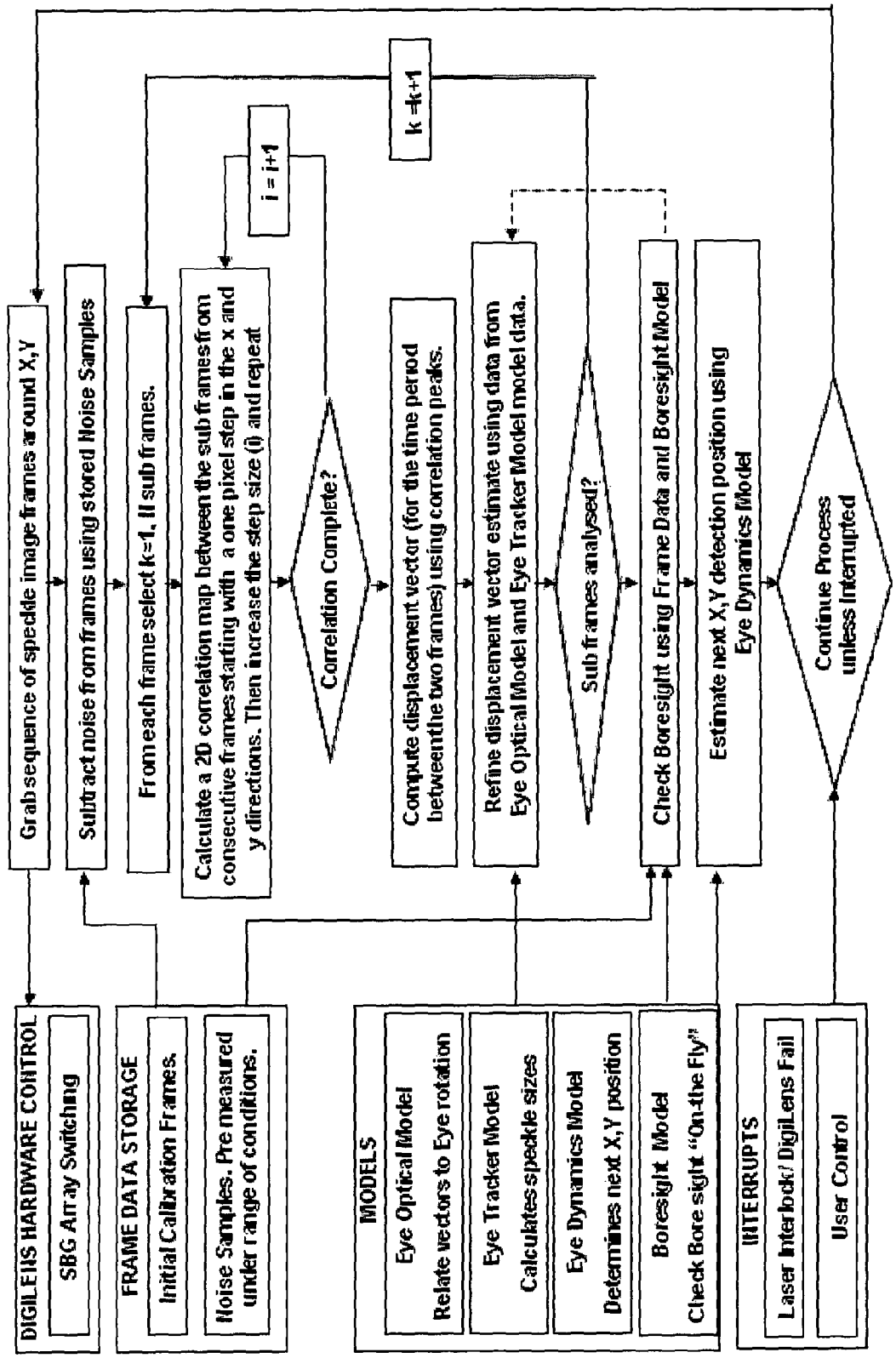
FIG. 30 is a flow chart showing the process for determining eye displacement vectors from the recorded speckle data.

The flow chart in FIG. 30 summarizes the process for determining eye displacement vectors from the recorded speckle data. The process relies on a database of frame data collected during initial calibration and noise characteristics. The calculation of the displacement vectors uses inputs from a suite of mathematical models that simulate the first order eye optics, the eye tracker optics and the eye dynamics. The process may be interrupted by the user or automatically when a DigiLens failure occurs. The process also includes DigiLens hardware control to enable X,Y addressing of DigiLens columns and readout elements.

The correlation process for obtaining the eye displacement vector from two detected frames in one embodiment may be summarised as follows. Each frame is subdivided into small sub frames. The sub-frame coordinates may be predefined or alternatively may be determined by an interactive scheme using the output from an Eye Dynamics Model. A 2D correlation map between the sub images from the two frames is calculated starting with a one pixel step in the x and y directions and repeat the calculation increasing the step size by one pixel at a time. Other statistical metrics may also be computed at this stage to assist in refining the calculation. We then repeat the correlation process for another selected frame region. A displacement vector is then computed using (for the time period between the two analysed frames) using the peaks of the correlation maps. Ideally the sub frames should be entirely within the corneal or retinal fields, the two being distinguished by their opposing directions. Data which does not yield clear separation of the two will be rejected) at this stage. The calculation is refined using data from an Eye Optical Model which models of the eye dynamics and an Eye Tracker Model which models the optical system. The verified displacement vector is used to determined the next search X,Y coordinates (ie SBG column, row) for the Eye Tracker using predicted gaze trajectory calculated using a Eye Dynamics Model. The basic ray optics used in the Eye Model in particular the relationship of the first order corneal and retinal reflection paths of the eye may be modelled using ray-tracing programmes such as ZEMAX. Standard eye models well known to those skilled in the art will be adequate for this purpose. Further models may be used to simulate speckle from the retina and the cornea. The Eye Dynamics Model carries out a statistical analysis of the displacement vectors from previous frames to determine the most optical next X,Y search location (ie the columns and readout elements to be activated in the DigiLens.

Reflection from the cornea has a strong secular component. Retinal reflection is more diffuse. The size of the corneal reflected angles would ordinarily require a large angular separation between the illumination and detection optical axes. This would make eye tracking using corneal reflections over large FOVs very difficult. The invention avoids the problem of imaging large reflection angles (and dealing with are lateral and vertical eye movements which can arise from slippage) by using matched scrolling illumination and detection. Hence the reflection angle becomes relatively small and can be approximated to: $\Psi \sim 2[(D/r-1)\Phi+d/r]$ where r is the cornea radius $\Phi$ is the eye rotation and D is the distance of the eye centre from the displaced centre of curvature of the cornea and d is the lateral displacement of the eye centre.

Initial calibration is carried out by directing the user to look at test targets at predefined points in the FOV. The bore-sighting process is illustrated in FIG. 32 which shows a flowchart (FIG. 32A) and a schematic illustrates of the initial calibration procedure (FIG. 32B). According to FIG. 31A the bore sighting procedure 400 comprises the following steps:

At step 401 present targets to the eye at location j;

At step 402 capture a series of frames at location j;

At step 403 store the capture frames;

At step 404 move to the next target position in the field of view (FOV).

At step 405 repeat the process while j is less than a predefined integer N; otherwise end the process (at step 406).

Figure 31:
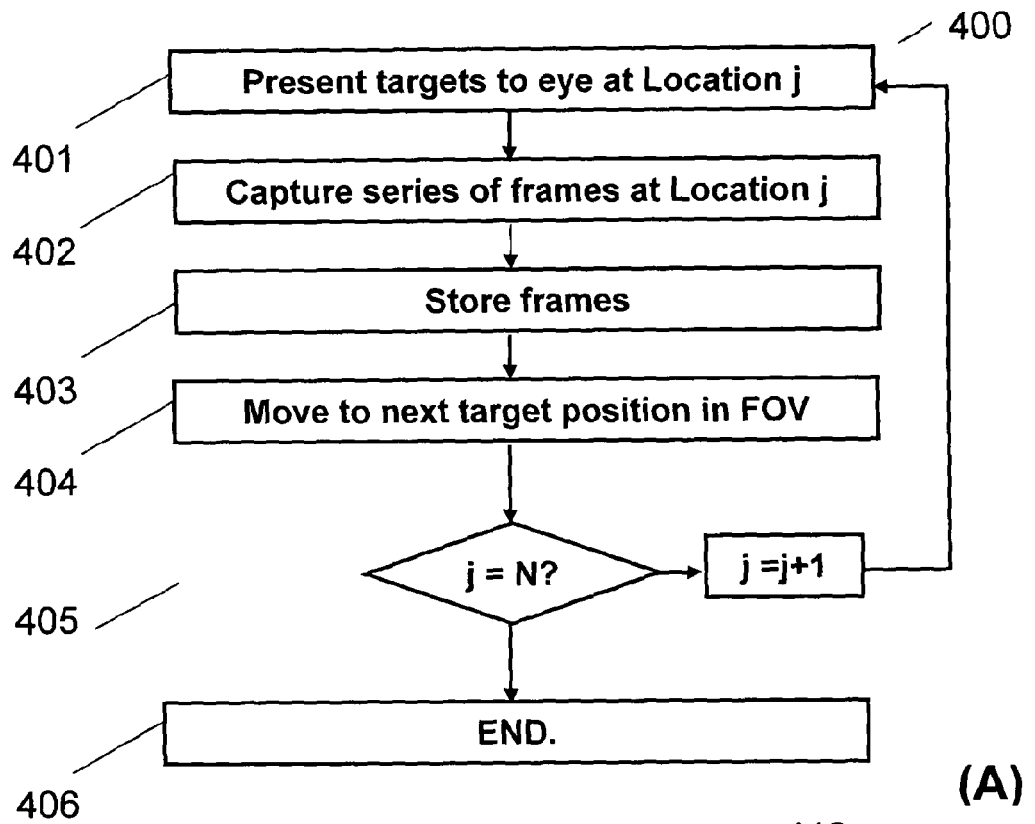
FIG. 31A is a flowchart for a calibration process for an eye tracker using common illumination and imaging gratings in one embodiment of the invention.
FIG. 31B is a schematic illustration of the initial calibration procedure used for an eye tracker in one embodiment of the invention
Figure 31:
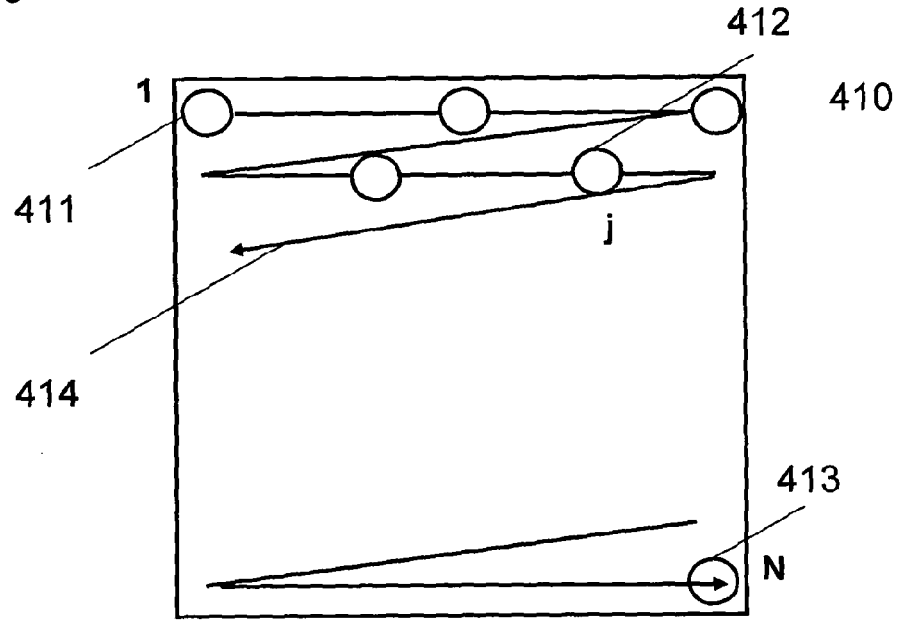

Referring to FIG. 31B we see that initial calibration will be carried by presenting targets (typically lights sources, resolution targets etc) to the viewer at different points $1 \leq j \leq N$ in the field of view 410 (the point also being labelled as 411-413) and capturing and storing frames of speckle pattern images at each location. The targets may be presented sequentially along the sweep path labelled by 414. However, other presentation schemes may be used. The stored frames will be processed to enhance SNR and extract statistical metrics (such as histograms, probability density functions for speckle size etc) for subsequent "on-the-fly" frame comparison. Each frame provides a "fingerprint" for the region of the FOV concerned. The signatures will vary in: relative positions of the corneal and retinal speckle pattern; speckle contrast; and the speckle size distribution (linked to optical magnification).

The optical design requires careful balancing of the high source flux needed to overcome throughput inefficiencies arising from the small collection angles, low transmission thorough the DigiLens and the low reflectivity of the eye (~2.5% at the surface of the cornea) with the requirement for eye-safe IR illumination levels. Typically, for applications in which the eye tracker is used for hours at a time under continuous IR exposure the eye irradiance should not exceed around 1 mW/cm2. The appropriate sstandards for eye safe infrared irradiance are well known to those skilled in the art. Since in our eye tracker we scroll the illumination the cornea and retina are not exposed to continuous IR exposure allowing higher exposures levels to be used leading to higher speckle contrast level and therefore higher SNR at the detector. In a SBG design there is the risk of a switching malfunction causing the laser beam scanning to freeze resulting in all of the available output laser power being concentrated into a small area of the eye. To overcome this problem a safety interlock will be provided to switch off the laser when no tracking activity has been detected for a predefined time—typically a few minutes. During this dead time the IR exposure may be allowed to increase significantly without exceeding the safety threshold, as indicate by the graph.

The following characteristics of the speckle image may also be used to assist the tracking of the eye use speckle: speckle grain size; speckle brightness (either individual or collective brightness); speckle shape; rate of change of any of the preceding characteristics with ocular movement; and relative directions of corneal and retinal bema displacements. It is further recognized that each of these aspects of the speckle image will be dependent on the illumination beam direction (scanning or static); the detection optics and the focal length of the imaging optics. The rate of change of the corneal versus retinal speckles will depend on the focal length.

As discussed the eye tracker measures and compare the signals from a wide range of "scanned" horizontal and vertical positions in front of the eye with calibration images recorded for the subject eye. Using the above speckle characteristics, the gaze direction may be determined to progressively greater levels of resolution and accuracy according to the number of characteristics measured. Advantageously, the user would calibrate the tracker by looking ahead and into the top/bottom left and right hand corners of the FOV. However, this may not be necessary in all embodiments of the invention. In addition by measuring the retinal and corneal speckles patterns and using more than one characteristic it is possible to determine the absolute gaze direction as well as the relative displacement.

Speckle tracking avoids the cost and complexity of implementing classical Purkinje imaging methods. Conventional iris image capture systems are an indicator the level of processing that will be required in an eye tracker. The iris image is typically acquired by a camera using infrared light in the 700 nm-900 nm band resolving in the region of 100-200 pixels along the iris diameter. The first step is usually to detect and remove stray light before proceeding to determine the boundaries of the iris. Typically the centers and radii of iris and pupil are approximated initially by applying a circular edge detector. High accuracy and rapid response times require high-performance and high-cost microprocessors that are beyond the scope of consumer products. Traditional image processing designs based on software are too slow. It is known that significant improvements may result from an an iris recognition algorithms based on a hardware-software co-design using low-cost FPGAs The system architecture consists of a 32-bit general purpose microprocessor and several dedicated hardware units. The microprocessor executes in software the less computationally intensive tasks, whereas the coprocessors speed-up the functions that have higher computational cost. Typically, depending on the function implemented, coprocessors speed-up the processing time by a factor greater than 10 compared to its software execution. However, the best latency achieved with hardware-software co-designs, is typically in the range 500-1000 ms. It should be noted that an eye tracker is a much more demanding proposition for an image processor. Detecting a clean iris image is only the first step. Applying the edge detection algorithms as the eye moves around the eye box will require several frames to be analysed adding to the overall latency.

Table 1 presents a comparison of an eye tracker based on a single SBG layer DigiLens as discussed above with a conventional image sensor comprising a camera and image recognition algorithms in the table below.

TABLE 1

Comparison of the present invention and a camera/image processing eye tracker.

|  | Speckle Eye Tracker | Camera and Image Processing |
|---|---|---|
| Detector | 16×16 IR Mouse Sensor | VGA CMOS Camera |
| Frame Rate | 2300 fps | 60 Hz |
| Detector Latency | 0.43 ms (for 16 × 16 pixel image frame) | 16.67 ms (for VGA frame) |

TABLE 1-continued

Comparison of the present invention and a camera/image processing eye tracker.

|  | Speckle Eye Tracker | Camera and Image Processing |
|---|---|---|
| Image Processing Latency | 4.3 ms. (10 frames using X-Y search algorithm). | Estimated: 500 ms.-1000 ms. (To apply feature recognition and tracking). |
| Total Eye Tracker Latency | ~5 ms. | ~500-1000 ms. |
| Relative Latency | 1 | VGA CMOS Camera |

The proposed eye tracker is compatible with many display applications in consumer products, avionics and other fields such as Augmented Reality by enabling the features of: wide field of view; large exit pupil; thin form factor; low inertia; and easy integration with near-eye display technologies.

It should be emphasized that the drawings are exemplary and that the dimensions have been exaggerated. For example thicknesses of the SBG layers have been greatly exaggerated.

In any of the above embodiments the substrates sandwiching the HPDLC layer may be planar, curved or formed from a mosaic of planar or curved facets.

An eye tracker based on any of the above-described embodiments may be implemented using plastic substrates using the materials and processes disclosed in PCT Application No.: PCT/GB2012/000680, entitled IMPROVEMENTS TO HOLOGRAPHIC POLYMER DISPERSED LIQUID CRYSTAL MATERIALS AND DEVICES.

Advantageously, the SBGs are recorded in a reverse mode HPDLC material in which the diffracting state of SBG occurs when an electric field is applied across the electrodes. An eye tracker based on any of the above-described embodiments may be implemented using reverse mode materials and processes disclosed in PCT Application No.: PCT/GB2012/000680, entitled IMPROVEMENTS TO HOLOGRAPHIC POLYMER DISPERSED LIQUID CRYSTAL MATERIALS AND DEVICES.

However, the invention does not assume any particular type of SBG.

A glass waveguide in air will propagate light by total internal reflection if the internal incidence angle is greater than about 42 degrees. Thus the invention may be implemented using transmission SBGs if the internal incidence angles are in the range of 42 to about 70 degrees, in which case the light extracted from the light guide by the gratings will be predominantly p-polarized.

Using sufficiently thin substrates the eye tracker could be implemented as a long clear strip appliqué running from the nasal to ear ends of a HMD with a small illumination module continuing laser dies, light guides and display drive chip tucked into the sidewall of the eyeglass. A standard index matched glue would be used to fix the display to the surfaces of the HMD.

The method of fabricating the SBG pixel elements and the ITO electrodes used in any of the above-described embodiments of the invention may be based on the process disclosed in the PCT Application No. US2006/043938, entitled METHOD AND APPARATUS FOR PROVIDING A TRANSPARENT DISPLAY.

The invention does not rely on any particular methods for introducing light from a laser source into the eye tracker and directing light scattered from the eye onto a detector. In the preferred embodiments of the invention gratings are used to perform the above functions. The gratings may be non switchable gratings. The gratings may be holographic optical elements. The gratings may be switchable gratings. Alternatively, prismatic elements may be used. The invention does not rely on any particular method for coupling light into the display.

It should be understood by those skilled in the art that while the present invention has been described with reference to exemplary embodiments, it is to be understood that the invention is not limited to the disclosed exemplary embodiments. Various modifications, combinations, sub-combinations and alterations may occur depending on design requirements and other factors insofar as they are within the scope of the appended claims or the equivalents thereof.

What is claimed is:

1. An eye tracker waveguide comprising:
   a light detector;
   an imaging grating comprising an array of switchable grating elements configured along a first waveguide path;
   an output grating; and
   an image sampling grating overlaying said output grating, comprising an array of switchable grating elements configured along a second waveguide path orthogonal to said first waveguide path,
   wherein said switchable grating elements are switchable between a diffracting state and a non-diffracting state and one grating element of each of said imaging grating and said image sampling grating is in said diffracting state at any time,
   wherein an instantaneous detection aperture of said waveguide is addressed by an image sampling grating element in said diffracting state and an imaging grating element in said diffracting state,
   wherein light reflected from said eye is coupled into said waveguide via said detection aperture into said first waveguide path, is coupled out of said first waveguide path by said output grating, and is coupled into said second waveguide path towards said detector by an image sampling grating element in said diffracting state.

2. The apparatus of claim 1 wherein said grating elements of said imaging grating are elongate with longer dimension aligned perpendicular to said first waveguide path.

3. The apparatus of claim 1 further comprising a source and an input grating for deflecting illumination light from said source into a third waveguide path; and an illumination grating for deflecting said illumination light out of said third waveguide path towards said eye.

4. The apparatus of claim 3 further comprising:
   an illumination sampling grating overlaying said input grating,
   said illumination grating comprising an array of switchable grating elements,
   said illumination sampling grating comprising an array of switchable grating elements configured along a fourth waveguide path orthogonal to said third waveguide path,
   wherein one grating element of each of said illumination grating and said illumination sampling grating is in said diffracting state at any time,
   wherein an instantaneous illumination aperture of said waveguide is addressed by an illumination sampling grating element in said diffracting state and an imaging grating element in said diffracting state,
   wherein light from said light source coupled into said waveguide via said input grating is coupled into said fourth waveguide path by an illumination sampling grating element in said diffracting state, is coupled into said third waveguide path and is coupled out of said waveguide towards said eye by an illumination grating element in said diffracting state.

5. The apparatus of claim 4 wherein said illumination sampling grating encodes at least one of optical power or diffusion.

6. The apparatus of claim 3 wherein said illumination grating abuts an upper or lower edge of said waveguide said edge parallel to said first waveguide path.

7. The apparatus of claim 3 wherein said illumination grating comprises first and second gratings disposed adjacent upper and lower edges of said waveguide said edges parallel to said first waveguide path.

8. The apparatus of claim 3 wherein said illumination grating is a linear array of elongate switchable beam deflection elements with longer dimension aligned perpendicular to said first waveguide path.

9. The apparatus of claim 3 wherein said imaging grating and said illumination grating are provided by a common grating, wherein said first waveguide path and said fourth waveguide path are provided by a common waveguide path along which said illumination light and said light reflected from said eye propagate in opposing directions.

10. The apparatus of claim 3 wherein said illumination grating or said illumination sampling grating encodes at least one of optical power or diffusion.

11. The apparatus of claim 1 wherein said imaging grating comprises a first array of switchable elongate beam deflection grating elements and an overlapping second array of switchable elongate beam deflection grating elements, said elements of said first and second arrays being disposed with their longer dimensions orthogonal.

12. The apparatus of claim 1 wherein at least one of said gratings is one of a switchable Bragg grating, a switchable grating recorded in a reverse mode holographic polymer dispersed liquid crystal, or a non switching Bragg grating.

13. The apparatus of claim 1 wherein said light reflected from said eye is speckle.

14. The apparatus of claim 1 wherein said eye surface is at least one of the cornea, lens, iris, sclera and retina.

15. The apparatus of claim 1 wherein said detector is a two dimensional array.

16. The apparatus of claim 1 wherein at least one of said imaging grating or said image sampling grating encodes at least one of optical power or light diffusion.

17. The apparatus of claim 1 wherein said detector is connected to an image processing apparatus for determining at least one spatio-temporal characteristic of an eye movement.

18. The apparatus of claim 1 wherein said light is in the infrared band.

19. The apparatus of claim 1 wherein said eye is illuminated by one of a laser or a light emitting diode.

20. The apparatus of claim 1 wherein said image sampling grating, comprises a one dimensional array of switchable grating elements.

* * * * *